United States Patent
Biwa et al.

(10) Patent No.: US 10,094,808 B2
(45) Date of Patent: Oct. 9, 2018

(54) METHOD AND DEVICE FOR EVALUATING POROSITIES INSIDE COMPOSITE MATERIAL

(71) Applicants: KAWASAKI JUKOGYO KABUSHIKI KAISHA, Kobe-shi, Hyogo (JP); KYOTO UNIVERSITY, Kyoto-shi, Kyoto (JP)

(72) Inventors: Shiro Biwa, Kyoto (JP); Akira Kuraishi, Kakamigahara (JP)

(73) Assignees: KAWASAKI JUKOGYO KABUSHIKI KAISHA, Hyogo (JP); KYOTO UNIVERSITY, Kyoto (JP)

( * ) Notice: Subject to any disclaimer, the term of this patent is extended or adjusted under 35 U.S.C. 154(b) by 170 days.

(21) Appl. No.: 15/107,809

(22) PCT Filed: Dec. 9, 2014

(86) PCT No.: PCT/JP2014/006147
§ 371 (c)(1),
(2) Date: Jun. 23, 2016

(87) PCT Pub. No.: WO2015/098010
PCT Pub. Date: Jul. 2, 2015

(65) Prior Publication Data
US 2016/0320353 A1  Nov. 3, 2016

(30) Foreign Application Priority Data
Dec. 25, 2013  (JP) .................................. 2013-266732

(51) Int. Cl.
*G01N 15/08*  (2006.01)
*G01N 29/04*  (2006.01)
(Continued)

(52) U.S. Cl.
CPC ......... *G01N 29/46* (2013.01); *G01N 15/0806* (2013.01); *G01N 15/088* (2013.01);
(Continued)

(58) Field of Classification Search
CPC ........ G01N 29/46; G01N 29/11; G01N 29/28; G01N 29/043; G01N 15/088;
(Continued)

(56) References Cited

U.S. PATENT DOCUMENTS 6,225,729 B1 * 5/2001 Izumi ..................... G10K 11/02
  310/334
6,234,025 B1 * 5/2001 Gieske ................. G01N 29/221
  73/629

(Continued)

FOREIGN PATENT DOCUMENTS

CN  104819922  *  8/2015
JP  H06-18488 A  1/1994
(Continued)

OTHER PUBLICATIONS

May 17, 2017 extended search report issued in European Patent Application No. 14874325.5.
(Continued)

*Primary Examiner* — J M Saint Surin
(74) *Attorney, Agent, or Firm* — Oliff PLC

(57) ABSTRACT

In a method of evaluating porosities, firstly, an ultrasonic wave is input in a thickness direction of a composite material to an incident surface which is one of the surfaces of the composite material having a multi-layer structure, and a reflective wave (whole reflective wave) is received from the incident surface. Then, the time-frequency analysis for the received whole reflective wave is performed. Thus, the temporal change information of the reflective wave (inter-layer reflective wave) included in the whole reflective wave
(Continued)

and reflected on an interlayer interface of the multi-layer structure, is obtained. This change information is suitably used to evaluate a distribution of porosities in the thickness direction of the composite material.

10 Claims, 12 Drawing Sheets

(51) Int. Cl.
  *G01N 29/28* (2006.01)
  *G01N 29/11* (2006.01)
  *G01N 29/46* (2006.01)

(52) U.S. Cl.
  CPC ........... *G01N 29/043* (2013.01); *G01N 29/11* (2013.01); *G01N 29/28* (2013.01); *G01N 2291/0231* (2013.01); *G01N 2291/0289* (2013.01); *G01N 2291/044* (2013.01)

(58) Field of Classification Search
  CPC ....... G01N 15/0806; G01N 2291/0231; G01N 2291/0289
  USPC .......................................................... 73/579
  See application file for complete search history.

(56) References Cited

U.S. PATENT DOCUMENTS

| | | | |
|---|---|---|---|
| 8,522,615 | B1 | 9/2013 | Brady et al. |
| 2004/0261530 | A1 | 12/2004 | Meier |
| 2007/0095141 | A1* | 5/2007 | Puckett ................. G01N 29/11 73/649 |
| 2007/0227249 | A1* | 10/2007 | Meier ................ G01N 29/0645 73/628 |
| 2008/0087093 | A1 | 4/2008 | Engelbart et al. |
| 2012/0170051 | A1* | 7/2012 | Edelmann .............. G01B 11/25 356/600 |
| 2012/0186349 | A1 | 7/2012 | Inoue |

FOREIGN PATENT DOCUMENTS

| | | |
|---|---|---|
| JP | H06-317568 A | 11/1994 |
| JP | 2008-233048 A | 10/2008 |
| JP | 2010-169558 A | 8/2010 |

OTHER PUBLICATIONS

Mar. 17, 2015 International Search Report issued in International Patent Application No. PCT/JP2014/006147.
Jun. 28, 2016 International Preliminary Report on Patentability issued in International Patent Application No. PCT/JP2014/006147.

* cited by examiner

METHOD AND DEVICE FOR EVALUATING POROSITIES INSIDE COMPOSITE MATERIAL

TECHNICAL FIELD

The present invention relates to a method and device for evaluating porosities (many minute vacancy defects which are dispersed) remaining inside a fiber-reinforced resin composite material. In particular, the present invention relates to a method and device for evaluating porosities, which can evaluate an uneven distribution or the like of the porosities contained in the composite material, in the thickness direction of the composite material, as well as the total amount of the porosities contained in the fiber-reinforced resin composite material.

BACKGROUND ART

In recent years, in the fields in which metal materials were commonly used in the past, fiber-reinforced resin composite materials (hereinafter these will be referred to as "composite materials") have been widely used. For example, a carbon fiber reinforced material (in general, referred to as carbon fiber reinforced plastics (CFRP)) formed by impregnating carbon fibers which are reinforced fiber material with a matrix resin including an epoxy resin or the like has a lighter weight and a higher strength than the metal materials do. For this reason, in recent years, the carbon fiber reinforced material has been widely used in the fields of sporting goods, industrial machines, vehicles (automobile, bicycle, etc.), aerospace, etc.

In general, a molded product comprising the composite material is obtained by laminating (stacking) plural sheets of prepreg together (sheets comprising a fiber reinforced material, impregnated with a matrix resin), and the resulting laminate is pressurized and heated to be cured in an autoclave.

Depending on a pressure applied to cure the uncured laminate or a temperature at which the laminate is heated, many minute vacancy defects called "porosities" emerge in a dispersed manner inside the composite material. If the porosities are present in a specified amount or more inside the composite material, this may lead to reduction of the structural strength of the composite material, in particular, in a case where the composite material is used in the field of aerospace, the structural strength requirements of the composite material is high, compared to a case where the composite material is used in other fields. Therefore, it is necessary to reduce the amount of porosities to a possible level. In view of this, when the composite material is manufactured, it is necessary to evaluate the porosities in a non-destructive manner.

Conventionally, as a technique for evaluating the defects of the composite material in the non-destructive manner, for example, there are an ultrasonic flaw detection method disclosed in Patent Literature 1, or an ultrasonic flaw detection device disclosed in Patent Literature 2. These techniques are intended for the composite material primarily used in the field of aerospace. In these techniques, an ultrasonic wave is input to the obverse surface of the composite material in a thickness direction, a reflective wave reflected on the reverse surface of the composite material and a transmissive wave measured on the reverse surface are measured, and the defects of the composite material are tested based on a degree to which the reflective wave or the transmissive wave is damped or the damping characteristics of the reflective wave or the transmissive wave.

CITATION LIST

Patent Literature

Patent Literature 1: Japanese Laid-Open Patent Application Publication No. Hei. 06-018488
Patent Literature 2: Japanese Laid-Open Patent Application Publication No. Hei. 06-317568

SUMMARY OF INVENTION

Technical Problem

However, in the techniques disclosed in Patent Literature 1 and Patent Literature 2, it is difficult to evaluate unevenness (non-uniformity) in a plate thickness direction, of the porosities contained in the composite material.

In the techniques disclosed in Patent Literature 1 and Patent Literature 2, the defects are tested based on the damping rate of the reflective wave reflected on the reverse surface of the composite material. The damping rate of the reflective wave results from reflection of material characteristics (or total amount material characteristics) integrated along the propagation path of the ultrasonic wave. Therefore, the total amount of the porosities contained in the whole of the composite material, in the thickness direction of the composite material, can be evaluated. However, it is difficult to evaluate the uneven state of the porosities in the thickness direction.

In other words, since the damping rate of the reflective wave fundamentally depends on the total amount of the porosities contained. In the composite material, in the techniques disclosed in Patent Literature 1 and Patent Literature 2, it cannot be identified whether the distribution of the porosities is even or uneven (uniform or non-uniform).

In recent years, in the field of aerospace, in a case where members made of the composite material are manufactured, a method in which a plurality of members are integrally molded simultaneously has spread. Among the members molded simultaneously in this manufacturing method, a degree to which the porosities emerge or are distributed are different. In the technique disclosed in Patent Literature 1 or Patent Literature 2, whether or not the members have the porosities can be detected, but the distribution of the porosities cannot be evaluated. For this reason, for example, in a case where the integrally molded product has the porosities in a specified amount or more, it is inevitably determined that the whole of the molded product including the member having a sufficient strength is unusable.

The present invention is directed to solving the above-described problem, and an object of the present invention is to provide a technique which is capable of evaluating the distribution of the porosities contained in the composite material, in the thickness direction of the composite material, as well as the total amount of the porosities.

Solution to Problem

To solve the above described problem, according to the present invention, a method of evaluating porosities contained in a composite material, comprises inputting an ultrasonic wave in a thickness direction of the composite material to an incident surface which is one of surfaces of the composite material and receiving a reflective wave from the incident surface, the composite material having a multi-layer structure which is obtained by laminating a plurality of plies of prepreg and curing the prepreg; and performing time-frequency analysis of a whole reflective wave to obtain temporal change information of an interlayer reflective wave, the temporal change information being used to evaluate a distribution of the porosities contained in the composite material, in the thickness direction of the composite material, the whole reflective wave being the reflective wave received, and the in tetramer reflective wave being a reflective wave included in the whole reflective wave and reflected on an interlayer interface of the multi-layer structure.

In accordance with this configuration, by performing the time-frequency analysis of the whole reflective wave, the temporal (time) change information of the interlayer reflective wave can be obtained. This change information includes information indicating damping of the reflective wave which is attributed to the porosities. Therefore, based on this change information, the distribution of the porosities contained in the composite material, in the thickness direction of the composite material, can be evaluated well.

In the above method of evaluating the porosities contained in the composite material, when an incident frequency of the ultrasonic wave which is used to evaluate a total amount of the porosities contained in the composite material based on damping of a bottom surface reflective wave reflected from a bottom surface which is the other surface of the composite material, is a standard frequency, the incident frequency of the ultrasonic wave may be set to be higher than the standard frequency.

In the above method of evaluating e porosities contained in the composite material, the incident frequency may be variable according to a thickness of the plies constituting the composite material.

In the above method of evaluating the porosities contained in the composite material, to estimate the distribution of the porosities contained in the composite material, the change information of the interlayer reflective wave received actually may be compared to evaluation information, and used as the evaluation information may be at least one of: simulated change information of the interlayer reflective wave, which is obtained by performing numeric value simulation which reproduces in a simulated manner the composite material containing the porosities which are modeled, and input of the ultrasonic wave and reception of the reflective wave, with respect to the composite material, and known information of the interlayer reflective wave, which is obtained by input of the ultrasonic wave and reception of the reflective wave, with respect to a test piece of the composite material containing the porosities which are known.

In accordance with this configuration, the change information obtained by the numeric value simulation is the evaluation information obtained by reproducing well the characteristics of the change information obtained by performing the time-frequency analysis of the interlayer reflective wave actually measured. The known information of the interlayer reflective wave is the evaluation information obtained from the test piece containing the known porosities. By comparing the change information based on the actual measurement to these evaluation information, the distribution of the porosities contained in the composite material can be evaluated accurately.

To solve the above described problem, according to the present invention, a device for evaluating porosities contained in a composite material, comprises an ultrasonic wave detection unit which inputs an ultrasonic wave in a thickness direction of the composite material to an incident surface which is one of surfaces of the composite material and receives a reflective wave from the incident surface, the composite material having a multi-layer structure which is obtained by laminating a plurality of plies of prepreg and curing the prepreg; and a time-frequency analyzing unit which performs time-frequency analysis of a whole reflective wave to obtain temporal change information of an interlayer reflective wave, the temporal change information being used to evaluate a distribution of the porosities contained in the composite material, in the thickness direction of the composite material, the whole reflective wave being the reflective wave received, and the interlayer reflective wave being a reflective wave included in the whole reflective wave and reflected on an interlayer interface of the multi-layer structure.

The device for evaluating the porosities contained in the composite material may comprise a display information generation unit which generates display information from the change information; and a display unit which displays the change information using the display information.

The device for evaluating the porosities contained in the composite material, may comprise: a porosity evaluation unit which estimates the distribution of the porosities contained in the composite material, by comparing the change information obtained by the time-frequency analyzing unit to evaluation information, and used as the evaluation information may be, at least one of simulated change information of the interlayer reflective wave and known information obtained in advance, of the interlayer reflective wave of the composite material, the simulated change information of the interlayer reflective wave being obtained by performing numeric value simulation which reproduces in a simulated manner, input of the ultrasonic wave and reception of the reflective wave, with respect to the composite material containing the porosities which are modeled, and the known information of the interlayer reflective wave being obtained by the input of the ultrasonic wave and reception of the reflective wave, with respect to a test piece of the composite material containing the porosities which are known.

The device for evaluating the porosities contained in the composite material, may comprise: at least one of an ultrasonic wave transmission/reception simulator which performs the numeric value simulation and an evaluation information database in which the plural evaluation information is stored, and the porosity evaluation unit may obtain the evaluation information from at least one of the ultrasonic wave transmission/reception simulator and the evaluation information database.

Advantageous Effects of Invention

With the above described configuration, the present invention has an advantage that it is possible to provide a technique capable of evaluating the distribution of the porosities contained in the composite material, in the thickness direction of the composite material, as well as the total amount of the porosities contained in the composite material.

DESCRIPTION OF EMBODIMENTS

Hereinafter, the preferred embodiments of the present invention will be described with reference to the drawings. Hereinafter, throughout the drawings, the same or corresponding components are identified by the same reference symbols, and will not be described repeatedly.

Embodiment 1

[Composite Material]
First of all, the composite material containing the porosities to be evaluated in the present invention will be specifically described with reference to FIGS. 1A to 1C. In the present invention, as described above, the term "porosities" means "many minute vacancy defects which are dispersed". Although the term "porosities" is sometimes meant to include the rate of the content of the vacancy defects, the term "porosities" refers to the defects themselves in the present embodiment.

Figure 1A:
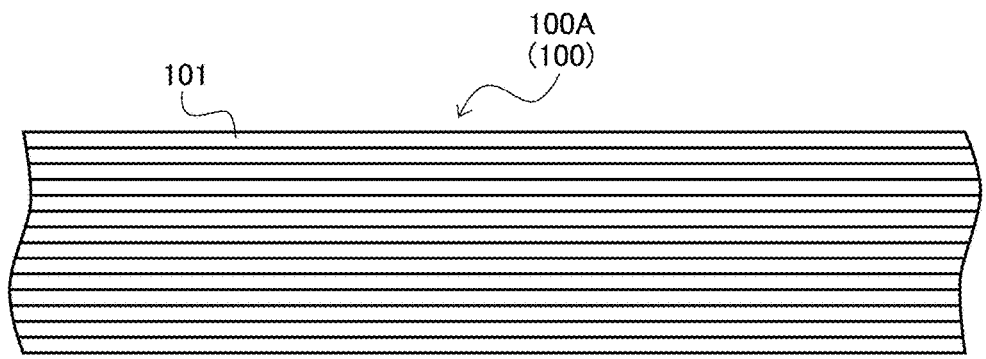
FIG. 1A is a cross-sectional view schematically showing an exemplary sound composite material containing no porosities, which is the composite material which is an evaluation target, of the present invention.
Figure 1B:
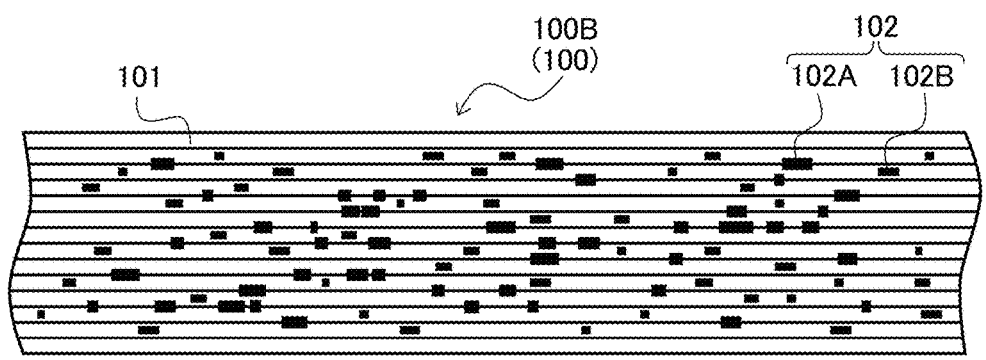
FIGS. 1B and 1C are cross-sectional views schematically showing exemplary defective composite materials, respectively, containing porosities.
Figure 1C:
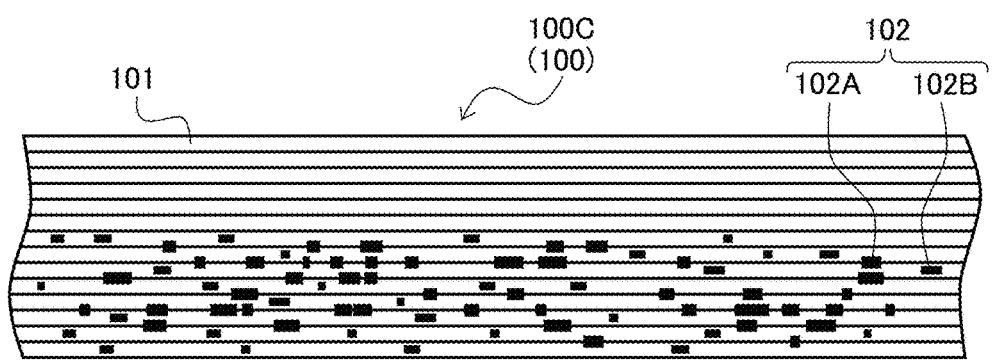

As shown in FIGS. 1A to 1C, each of composite materials 100A to 100C has a multi-layer structure including a plurality of plies 101 which are laminated (stacked). Each ply 101 fundamentally comprises a fiber material which is a reinforcement material and a thermosetting resin composition which is a matrix material. The plurality of plies 101 each comprising the fiber material and the thermosetting resin composition are laminated stacked) and integrated into each of the composite materials 100A to 100C.

Among the composite materials 100A to 100C, the sound (healthy) composite material 100A of FIG. 1A has an ideal state in which the composite material 100A contains no defects therein. The defective composite material 100B of FIG. 1B or the defective composite material 100C of FIG. 1C contains a plurality of porosities 102 (minute vacancy defects) inside. As shown in FIG. 1B or 1C, the porosities 102 include porosities 102A which are present between the plies 101 and porosities 102B contained inside the plies 101. The defective composite material 100B of FIG. 1B has a porosity distribution in which the porosities 102A and the porosities 102B are relatively dispersed. In contrast, the defective composite material 100C of FIG. 1C has a porosity distribution in which the porosities 102A and the porosities 102B are present unevenly on one side (closer to one of the surfaces of the defective composite material 100C).

Although the composite materials 100A to 100C are shown in FIGS. 1A to 1C as flat plate members, respectively, for the sake of convenience, composite materials which are actual evaluation targets are molded products having various shapes corresponding to uses. In the present embodiment, the term "composite material" refers to "a molded product made of the composite material" as an evaluation target, as well as the composite material as "a material," Also, hereinafter, when the term "composite material" is used in the specification without discrimination among the sound composite material 100A, the defective composite material 100B and the defective composite material 100C, this will be expressed as "the composite material 100."

Typically, the composite material 100 is manufactured in such a manner that the plies of prepreg are laminated (stacked) (ply lay-up) together to form a desired shape, and the prepreg is heated and pressurized to be cured in an autoclave (pressure vessel). The prepreg includes a fiber material impregnated with a thermosetting resin composition, which is partially cured.

The thermosetting resin used in the composite material 100 is not particularly limited. As the thermosetting resin used in the composite material 100, the thermoplastic resin known in the field of the composite material, for example, an epoxy resin, a bis maleimide resin, a vinylester resin, an unsaturated polyester resin, a phenol resin, and a silicone resin. Among these resins, one kind of resin or a combination of plural kinds of these resins may be used.

The thermosetting resin may include various additive agents such as a solvent, a curing agent, a curing accelerator, a stabilization agent, and an antistatic agent. Therefore, the matrix material included in the composite material 100 may comprise only one or more kinds of thermosetting results), or the thermosetting resin composition containing other components. Therefore, in the present embodiment, the "thermosetting resin composition" includes a resin mixture comprising plural kinds of thermosetting resins or one kind of thermosetting resin, as well as the composition including the thermosetting resin and other components.

The fiber material used in the composite material 100 is not particularly limited so long as the fiber material is capable of reinforcing the molded product (composite material) when this fiber material is used with the thermosetting resin composition. Specifically, for example, there are carbon fibers, polyester fibers, PBO (poly-phenylene benzobisoxazole) fibers, boron fibers, aramid fibers, glass fibers, silica fibers (quarts fibers), silicon carbide (SiC) fibers, nylon fibers, etc., Among these fiber materials, one kind of fiber material, or a combination of plural kinds of these fiber materials may be used. For example, in the field of aircraft, the carbon fibers are suitably used. Further, the length, diameter, and the like of the fiber material are not particularly limited, and may be appropriately set according to the uses of the composite material 100.

In the composite material 100, a ratio between the fiber material and the thermosetting resin composition is not particularly limited, and can be appropriately set according to the uses, use conditions, etc. Moreover, the composite material 100 may contain other known materials, in addition to the fiber material and the thermosetting resin composition.

The composite material 100 of the present invention is used in various fields such as sporting goods, industrial machines, vehicle, aerospace, etc. . . . , and its use is not particularly limited. A typical use of the composite material 100 is in the field of aerospace such as aircraft members.

In the field of aerospace, the requirement of a strength or the like is higher than in other fields. The strength or the like is not uniformly defined for all members in the field of aerospace. There is a difference in permissibility of reduction of a strength, depending on the kind or role of the member. As described above, in the aerospace field, the method in which the plurality of members are integrally molded simultaneously can be used, when the composite material members are manufactured. Therefore, the porosities are not evenly present in the members molded simultaneously. In the present invention, the porosities of each of the aircraft members can be evaluated well.

[Porosity Evaluation Method]

Next, the porosity evaluation method according to Embodiment 1 will be specifically described with reference to FIGS. 2 and 3A to 3C.

In the porosity evaluation method, the total amount of the porosities 102 contained in the composite material 100 can be evaluated, and the uneven (non-uniform) distribution of the porosities 102 in the thickness direction of the composite material 100, or the like can be evaluated. For example, it is supposed that regarding the defective composite material 100B of FIG. 1B and the defective composite material 100C of FIG. 1C, the distribution of the porosities 102 contained therein is different but the total amount of the porosities 102 is substantially equal. In this case, with a conventional porosity evaluation method, a difference between the sound composite material 100A and the defective composite material 100B or the defective composite material 100C can be evaluated, but it is virtually difficult to evaluate a difference between the defective composite material 100B and the defective composite material 100C, which contain the porosities 102 in an equal amount.

Figure 2:
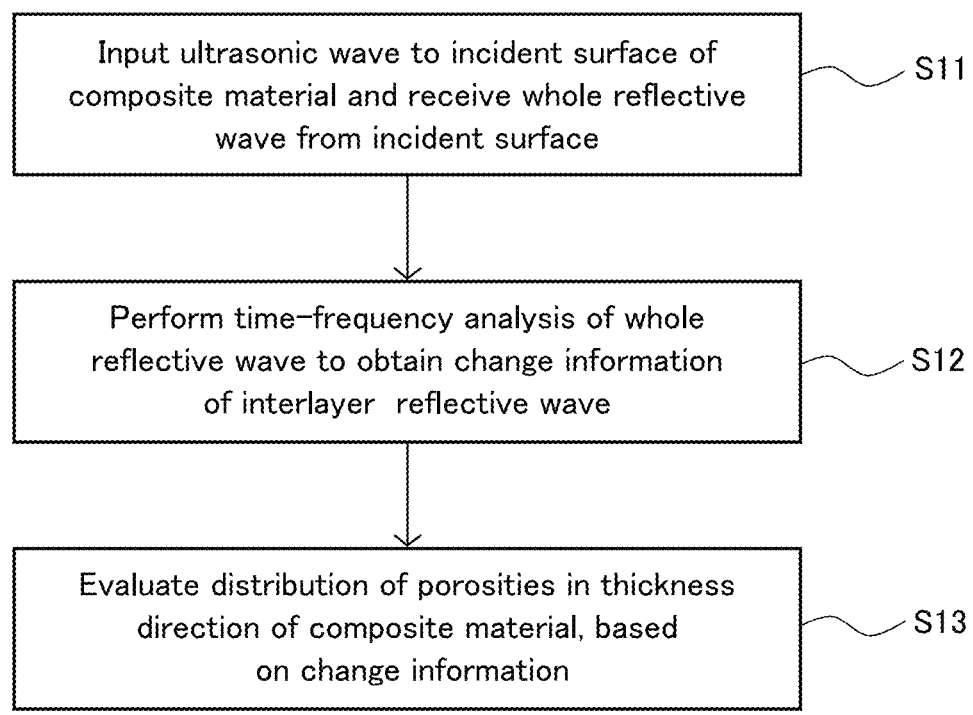
FIG. 2 is a view showing the steps of an exemplary porosity evaluation method of the composite material according to Embodiment 1 of the present invention.

In contrast, in the porosity evaluation method according to the present embodiment, as shown in FIG. 2, time-frequency analysis is performed for the reflective wave of an ultrasonic wave which is input to the composite material 100. This makes it possible to evaluate the distribution of the porosities 102, or the like, as to whether or not the porosities 102 are present unevenly (non-uniformly) inside the composite material 100. This porosity evaluation method be schematically described, using, for example, the defective composite material 100B or 100C of a three-layer structure of FIG. 3A, or the defective composite material 100B or 100C of a five-layer structure of FIGS. 3B and 3C.

Figure 3A:
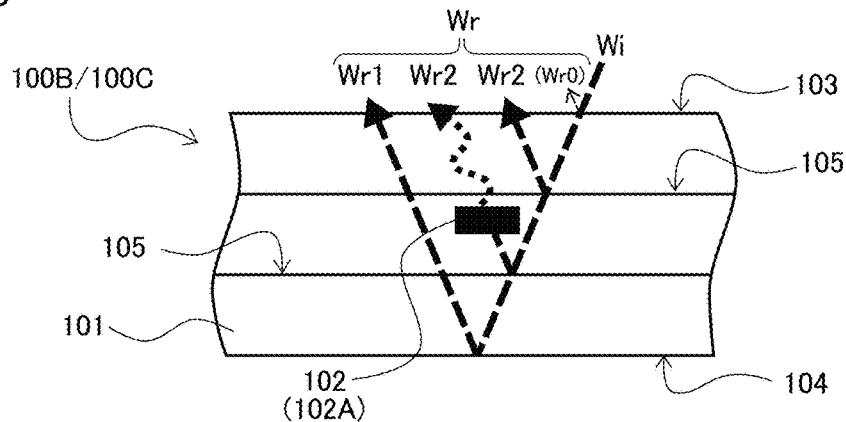
FIG. 3A is a schematic view for explaining a reflective wave of an ultrasonic wave input to the composite material to evaluate the porosities.
Figure 3B:
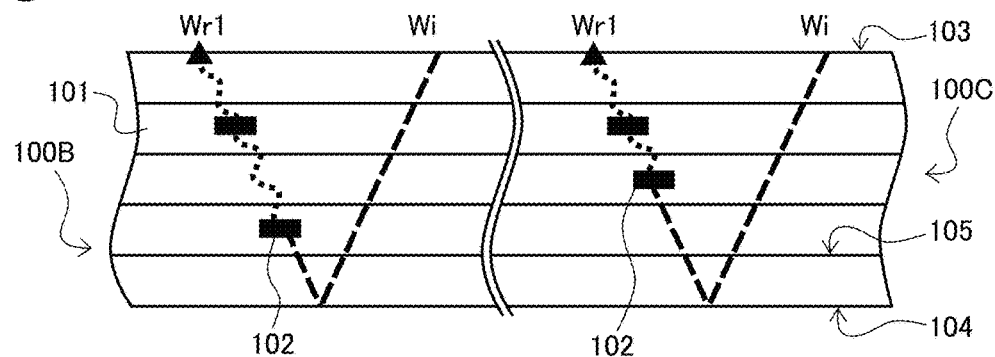
FIGS. 3B and 3C are schematic views for explaining damping of the reflective wave due to the porosities.
Figure 3C:
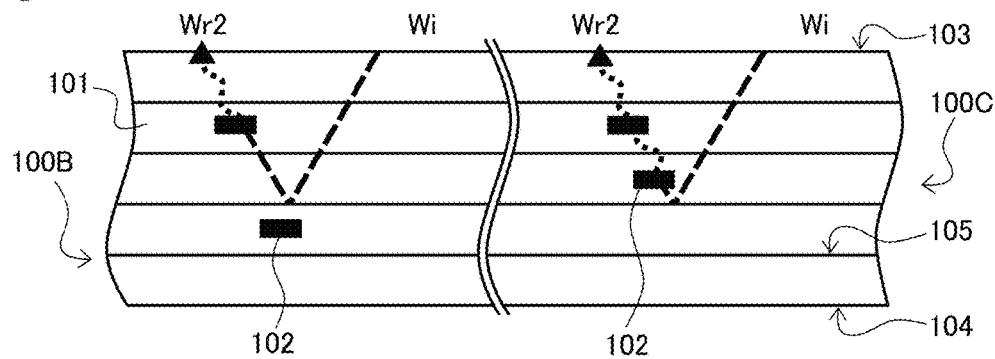

In the examples of FIGS. 3A to 3C, the surface (e.g., obverse surface) on one side of the composite material 100 is an incident surface 103, the surface (e.g., reverse surface) on the other side of the composite material 100 is a bottom surface 104, and an interface between the plies 101 is an interlayer interface 105 of a multi-layer structure. In the examples of FIGS. 3A to 3C, for easier understanding of the description, only the porosity 102 (the porosity 102B of FIGS. 1A and 1C) present inside each ply 101 is shown, and the porosity 102 (the porosity 102A of FIGS. 1B and 1C) present at the interface between the plies 101 is not shown.

In the examples of FIGS. 3A to 3C, when the ultrasonic wave is input to the incident surface 103 of the composite material 100, a portion of an incident wave Wi of the ultrasonic wave is reflected on the bottom surface 104 and becomes a bottom surface reflective wave Wr1. In addition, a portion of the incident wave Wi of the ultrasonic wave is reflected on the interlayer interface 105 before it reaches the bottom surface 104 and becomes an interlayer reflective wave Wr2. Therefore, a reflective wave Wr received in the incident surface 103 includes the bottom surface reflective wave Wr1 and the interlayer reflective wave Wr2. For easier understanding of the description, all of the reflective waves Wr received in the incident surface 103 will be referred to as "whole reflective wave Wr."

The whole reflective wave Wr is the reflective wave of the ultrasonic wave received (detected) at a position (position which is closer to the incident surface 103) on the incident surface 103 side of the composite material 100. As indicated by a thin broken line of FIG. 3A, the whole reflective wave Wr includes an obverse surface reflective wave Wr0 in addition to the bottom surface reflective wave Wr1 and the interlayer reflective wave Wr2. The obverse surface reflective wave Wr0 is a reflective wave resulting from the reflection of the ultrasonic wave on the incident surface 103.

In the case where the ultrasonic wave is input to the incident surface 103 of the composite material 100, actual behavior of the ultrasonic wave becomes complicated. Specifically, when the ultrasonic wave is input to the incident surface 103 of the composite material 100, in a direction perpendicular to the incident surface 103, this ultrasonic wave is scattered by the same porosity 102 in a path through which the ultrasonic wave travels in a downward direction toward the bottom surface 104, and in a path through which the ultrasonic wave travels in an upward direction toward the incident surface 103 after it is reflected on the bottom surface 104, and thereby damped. However, in the examples of FIGS. 3A to 3C, for easier understanding of the description only a case where the ultrasonic wave is scattered in the path through which the ultrasonic wave travels in the upward direction is shown. Therefore, the incident wave Wi, the bottom surface reflective wave Wr1, and the interlayer reflective wave Wr2 are assumed as simple arrows and indicated by the bold broken lines. In the examples of FIGS. 3A to 3C, the angles formed by the incident wave Wi, and the reflective waves Wr0, Wr2 are shown for easier understanding of the description, and do not represent the actual behaviors of the ultrasonic wave.

In the example of FIG. 3A, as the interlayer reflective wave Wr2, two interlayer reflective waves Wr2 are shown, which are the interlayer reflective wave Wr2 reflected on the interlayer interface 105 between the plies 101 of the first and second layers from the top, and the interlayer reflective wave Wr2 reflected on the interlayer interface 105 between the plies 101 of the second and third layers from the top. Of these two interlayer reflective waves Wr2, the latter interlayer reflective wave Wr2 is indicated by a sinuous dotted-line arrow. This interlayer reflective wave Wr2 is such that a portion of the incident wave Wi is scattered in the porosity 102 present in the ply 101 of the second layer, and thereby damped. This damped interlayer reflective wave Wr2 is shown in the same manner in the examples of FIGS. 3B and 3C.

In the examples of FIGS. 3B and 3C, shown on a left side is the defective composite material 100B in which the porosities 102 are dispersed, while shown on a right side is the defective composite material 100C in which the porosities 102 are present unevenly at a position which is closer to the incident surface 103. In the examples of FIGS. 3B and 3C, two porosities 102 are shown on each of the right and left sides, in the defective composite material 100B, the porosities 102 are present in the ply 101 of the second layer from the top and in the ply 101 of the second layer from the bottom (fourth ply 101 from the top), in the defective composite material 100C, the porosities 102 are present in the ply 101 of the second layer from the top and in the ply 101 of the third layer from the top.

In the porosity evaluation method of FIG. 2, the ultrasonic wave is input to the incident surface 103 of the composite material 100 in the thickness direction of the composite material 100 (see the incident wave Wi of FIG. 3A), and the whole reflective wave Wr of the ultrasonic wave is received from the incident surface 103 (step S11). Then, the received whole reflective wave Wr is subjected to the time-frequency analysis, to obtain the temporal (time) change information of the interlayer reflective wave Wr2 contained in the whole reflective wave Wr (step S12). Then, based on the obtained change information, the distribution of the porosities 102 in the thickness direction of the composite material 100 is evaluated (step S13).

In the conventional general porosity evaluation method, the porosities 102 are evaluated based on the damping rate (or damping characteristics or the like) of the bottom surface reflective wave Wr1. Thus, only the total amount of the porosities 102 is substantially evaluated. For example, in the example of FIG. 39, in the defective composite materials 100B, 100C, which are schematically shown, a portion of the bottom surface reflective wave Wr1 is scattered by the two porosities 102, thereby is damped, and reaches the incident surface 103.

For this reason, the damping rate of the bottom surface reflective wave Wr1 reflects the total amount of the porosities 102 in the thickness direction of the composite material 100, but does not well reflect a difference in the distribution of the porosities 102 in the thickness direction of the composite material 100. Therefore, in the evaluation based on only the damping rate of the bottom surface reflective wave Wr1, the difference in the distribution of the porosities 102 in the thickness direction of the composite material 100 cannot be taken into account. In other words, when only the damping rate of the bottom surface reflective wave Wr1 is measured, a difference between the defective composite material 100B in which the porosities 102 are dispersed and the defective composite material 100C in which the porosities 102 are present unevenly at a position which is closer to the incident surface 103 cannot be evaluated properly.

In contrast, in the example of FIG. 3C, the interlayer reflective wave Wr2 reflected on the interlayer interface 105 between the third and fourth layers is schematically shown. In the defective composite material 100B on a left side of FIG. 3C, the interlayer reflective wave Wr2 is not scattered by the porosity 102 located to be closer to the bottom surface 104 but is scattered only by the porosity 102 located to be closer to the incident surface 103. Therefore, the damping rate corresponds to one porosity 102. In contrast, in the defective composite material 100C on a right side of FIG. 3C, the interlayer reflective wave Wr2 is scattered by the two porosities 102 located to be closer to the incident surface 103. Therefore, the damping rate corresponds to the two porosities 102. For this reason, in the example of FIG. 3C, the damping rate of the interlayer reflective wave Wr2 of the defective composite material 100C is higher than that of the interlayer reflective wave Wr2 of the defective composite material 100B.

The interlayer reflective wave Wr2 is also generated on the interlayer interface 105 between the first and second layers, between the second and third layers, and between the fourth and fifth layers, in addition to the interlayer interface 105 between the third and fourth layers. Actually, the interlayer reflective wave Wr2 does not travel as the simple arrows of FIGS. 3B and 3C, but travels while repeating reflection and transmission on the interlayer interface 105 between the layers of the defective composite material 100B or the defective composite material 100C.

By performing the time-frequency analysis for the whole reflective wave Wr, a temporal change in each of frequency components included in the whole reflective wave Wr can be captured. In view of this, if a temporal change (damping) of the frequency component corresponding to the interlayer reflective wave Wr2 is obtained as change information, then it becomes possible to evaluate the distribution of the porosities 102 in the thickness direction of the defective composite material 100B or 100C, based on this change information. This change information is not particularly limited so long as this change information can be obtained as a result of the time-frequency analysis and can be used to evaluate the distribution of the porosities 102. For example, in an example which will be described later, a continued oscillation in a characteristic frequency range is obtained as the change information. This frequency range is suitably varied depending on the structure (number of layers, thickness, shape of molded product, etc.) of the composite material 100, and is not limited to a particular frequency range.

Although in the example of FIG. 3B or 3C, the composite material 100 is schematically shown as having the five-layer structure, the composite material 100 actually has a multi-layer structure comprising several tens to one hundred or more layers. For this reason, when the ultrasonic wave is input to the composite material 100 having the multi-layer structure, the interlayer reflective wave Wr2 is generated in each of many interlayer interfaces 105. Since the interlayer reflective wave Wr2 is generated within the whole of the composite material 100 in the thickness direction, compared to the bottom surface reflective wave Wr1, generated only in the bottom surface 104, the damping rate of the interlayer reflective wave Wr2 is varied. By utilizing the interlayer reflective wave Wr2, the change information including the states of the plies 101 included in the multi-layer structure can be obtained. In this way, various information can be obtained. As a result, the distribution of the porosities 102 inside the composite material 100 can be evaluated in more detail.

The frequency of the ultrasonic wave (incident wave Wi) is not particularly limited, and a frequency range known in the field of the ultrasonic flaw detection can be selected. In the present invention, unlike the conventional porosity evaluation method which pays attention to the damping of the bottom surface reflective wave Wr1, an attention is paid to the interlayer reflective wave Wr2. For this reason, a frequency range in which the interlayer reflective wave Wr2 is easily received in the incident surface 103 is preferably selected. Specifically, when an incident frequency (frequency used to evaluate the total amount of the porosities 102 based on the damping of the bottom surface reflective wave Wr1) in the conventional porosity evaluation method, is for example, a "standard frequency", an incident frequency in the porosity evaluation method of the present invention may be set to be higher than the standard frequency.

In the field of the ultrasonic flaw detection, it is known that if the wavelength of the ultrasonic wave is too short with respect to a propagation distance, the damping of the ultrasonic wave becomes great and the reflective wave (in particular, the bottom surface reflective wave Wr1) cannot be received well. In light of this, in the conventional porosity evaluation method, a relatively low frequency range is selected as the incident frequency to prevent the damping from becoming great even when the ultrasonic wave travels back and forth through the whole of the composite material 100, in the thickness direction of the composite material 100. In contrast, in the present invention, based on an idea which is the reverse of a technical common sense in the conventional porosity evaluation method, a relatively high frequency is selected. This makes it easier to obtain the interlayer reflective wave Wr2 which is good from each of the interlayer interfaces 105.

For example, if the incident frequency is set higher at a level in which the bottom surface reflective wave Wr1 cannot be received well, there is a possibility that the bottom surface reflective wave Wr1 from the bottom surface 104, or the good interlayer reflective wave Wr2 from the interlayer interface 105 which is closer to the bottom surface 104 cannot be obtained. However, in the evaluation of the distribution of the porosities, the interlayer reflective wave Wr2 may be preferentially received from the interlayer interface 105 which is closer to the incident surface 103. For this reason, as the incident frequency, a frequency range which is higher than that in the conventional porosity evaluation method can be selected and set.

As described above, the incident wave Wr1 is scattered by the porosity 102 located closer to the incident surface 103 and damped, so that the incident wave Wi becomes the interlayer reflective wave Wr2. Therefore, in the present invention, as described above, the interlayer reflective wave Wr2 which is closer to the incident surface 103 is preferentially obtained. On the other hand, if the incident frequency is set to be lower to obtain the bottom surface reflective wave Wr1 or the interlayer reflective wave Wr2 from the interlayer interface 105 which is closer to the bottom surface 104, it is likely that the good interlayer reflective wave Wr2 cannot be received from the interlayer interface 105 which is closer to the incident surface 103.

The incident frequency at which the interlayer reflective wave Wr2 can be received well from each of the interlayer interfaces 105 may be set according to the thickness of the plies 101 included in the composite material 100. The depth of a region in the thickness direction of the composite material 100, from which the interlayer reflective wave Wr2 can be received, is determined depending on the conditions such as the material of the composite material 100. For example, if the interlayer reflective wave Wr2 from a region with a depth which is about half of the whole thickness of the composite material 100 can be received, then the interlayer reflective waves Wr2 corresponding to the whole of the composite material 100 in the thickness direction can be received. In other words, if the interlayer reflective wave Wr2 is received from the obverse surface which is the incident surface 103 and then is received from the reverse surface which is the incident surface 103 in a state in which a positional relationship between the obverse surface and the reverse surface is reversed, the distribution of the porosities 102 can be evaluated for the whole of the composite material 100 in the thickness direction.

In the present invention, the total amount of the porosities 102 may be evaluated as well as the distribution of the porosities 102. As described above, in the present invention, the interlayer reflective wave Wr2 from the interlayer interface 105 which is closer to the incident surface 103 is preferentially received. Therefore, the bottom surface reflective wave Wr1 is fundamentally unnecessary. However, of course, in the evaluation of the total amount of porosities, a frequency range in which both of the interlayer reflective wave Wr2 and the bottom surface reflective wave Wr1 can be received well, may be selected.

In the present invention, the incident frequency is preferably variable depending on the thickness of the plies 101 included in the composite material 100. Since the composite material 100 which is actually evaluated is the molded product having a specified shape, the thickness (or the number of layers) of a single molded product is sometimes different. In view of this, by varying the incident frequency, the porosities of composite materials 100 of various shapes or uses can be generally evaluated.

The change method of the incident frequency is not particularly limited. The frequency of the ultrasonic wave which is used as the incident wave Wi may be set to a suitable frequency particular frequency is selected). In the present embodiment, the ultrasonic wave in a wide bandwidth including a suitable frequency corresponding to the conditions may be used as the incident wave Wi. This will be specifically described.

It may be said that a case where the interlayer reflective waves Wr2 are noticeably generated is a case where the phases of the interlayer reflective waves Wr2 from the regions (interlayer regions) each of which is between the plies 101 of the composite material 100 substantially conform to each other. In view of this, a case where all of the phases of the interlayer reflective waves Wr2 from the interlayer regions conform to each other is assumed, and the condition for realizing this will be roughly reviewed. When an ultrasonic wave propagation (transit) speed in the thickness direction of the ply 101 is c, the thickness of the ply 101 is h, and the frequency (incident frequency) of the incident wave Wi is f, and the wavelength of the incident wave Wi is λ, a relationship among c, h, f and λ can be approximately calculated according to the following formula (1):

$$\lambda = c/f = 2h \tag{1}$$

Therefore, the incident frequency f can be expressed as the following formula (2) using the ultrasonic wave propagation speed c, and the thickness h of the ply 101:

$$f = c/(2h) \tag{2}$$

It is known that in the case of the ply 101 made of the CFRP, a typical value of the ultrasonic wave propagation speed c (longitudinal wave propagation speed is about 3,000 m/s. Therefore, from the ultrasonic wave propagation speed c=3,000 m/s and the thickness h of the ply 101, the incident frequency f can be approximately calculated based on the following formula (2). For example, when the thickness h of the ply 101 made of CFRP is 0.15 mm, its incident frequency f can be approximately calculated as 10.0 MHz. Or, when the thickness h of the ply 101 made of CFRP is 0.19 mm, its incident frequency f can be approximately calculated as 7.9 MHz. Or, when the thickness h of the ply 101 made of CFRP is 0.40 mm, its incident frequency f can be approximately calculated as 3.8 MHz.

In a case where transmission and reception of the ultrasonic wave is actually measured, the ultrasonic wave in a relatively wide bandwidth including the frequency (suitable frequency) satisfying the formula (2) like the above-described approximately calculated value may be selected and the ultrasonic wave which is used as the incident wave Wi may be used. The ultrasonic wave in such a wide bandwidth is input to the composite material 100, at least the interlayer reflective wave Wr2 is received, and the time-frequency analysis for the interlayer reflective wave Wr2 is performed. Thus, it becomes possible to confirm that the interlayer reflective wave Wr2 is noticeably generated in a frequency range which is near the suitable frequency.

[Porosity Evaluation Device]

The specific configuration for carrying out the porosity evaluation method according to the present embodiment is not particularly limited. Now, an example of a typical porosity evaluation device (porosity evaluation device according to Embodiment 1) for carrying out the porosity evaluation method according to the present embodiment will be specifically described with reference to FIGS. 4 and 5.

Figure 4:
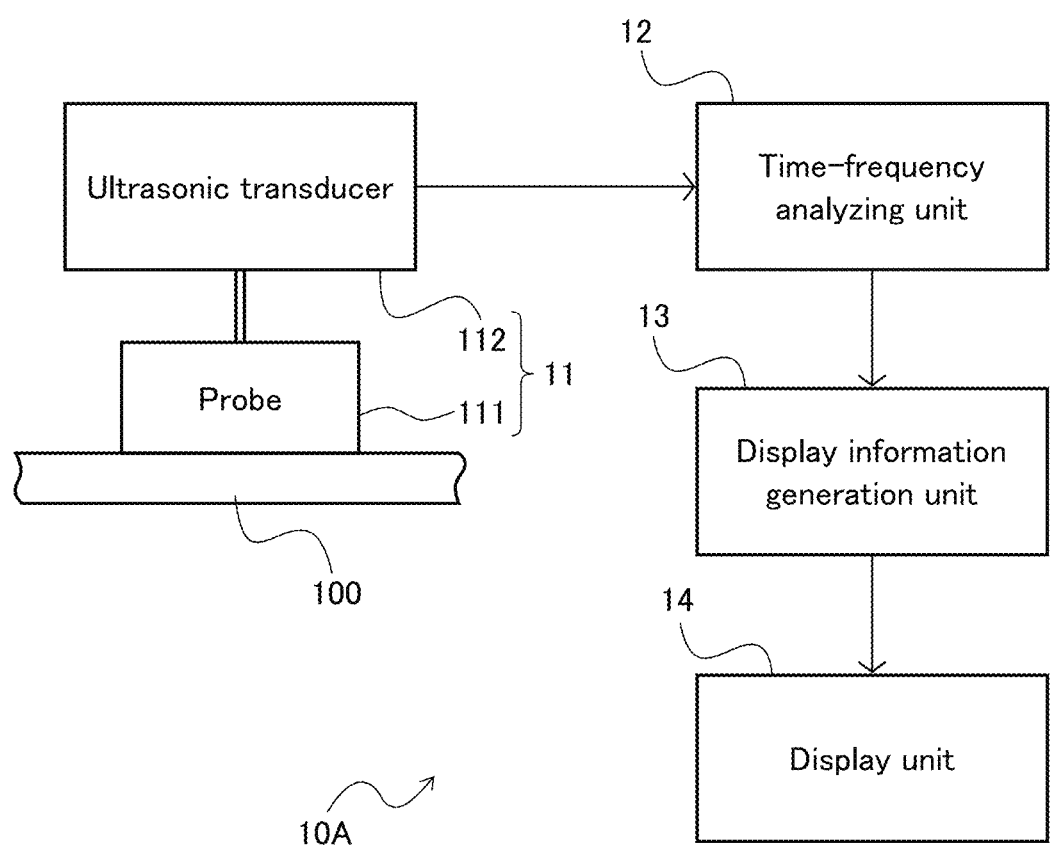
FIG. 4 is a block diagram schematically showing an exemplary porosity evaluation device used to perform the porosity evaluation method of FIG. 2.

As shown in FIG. 4, a porosity evaluation device 10A according to the present embodiment includes an ultrasonic wave detection unit 11, a time-frequency analyzing unit 12, a display information generation unit 13, and a display unit 14.

The ultrasonic wave detection unit 11 includes a probe 111, and an ultrasonic transducer (transmitter/receiver) 112. The ultrasonic wave detection unit 11 inputs the ultrasonic wave in the thickness direction to the incident surface 103 which is one of the surfaces of the composite material 100, and receives the whole reflective wave Wr from the incident surface 103. The specific configuration of the ultrasonic wave detection unit 11 is not particularly limited, and a configuration which is known in the field of the ultrasonic flaw detection may be suitably used.

The ultrasonic wave detection unit 11 is preferably configured to change the incident frequency. From among several kinds of probes 111 which are different from each other in nominal center frequency, a suitable probe 111 may be selected and used, according to the conditions material quality, thickness, or the like) of the composite material 100. The ultrasonic transducer 112 may include a configuration (frequency adjusting unit) for changing the incident frequency. Or, the porosity evaluation device 10A may include the frequency adjusting unit as a unit separate from the ultrasonic transducer 112.

Although the probe 111 is shown as being in direct contact with the composite material 100 in the block diagram of FIG. 4, it is necessary to interpose a buffering material (delay material) between the transmission/reception surface of the ultrasonic wave and the incident surface 103. The specific kind of the buffering material is not particularly limited. Water is used in common cases, as in the example which will be described later. Therefore, the ultrasonic wave detection unit 11 may be configured to transmit and receive the ultrasonic wave in a state in which the composite material 100 is immersed in the water. The buffering material is not necessarily limited to the water so long as the material is capable of receiving the waveform of the obverse surface reflective wave Wr0 and the waveform of the interlayer reflective wave Wr2 following the obverse surface reflective wave Wr0. A known resin may be used as the buffering material.

The time-frequency analyzing unit 12 performs the time-frequency analysis of the whole reflective wave Wr received in the ultrasonic wave detection unit 11 from the incident surface 103 of the composite material 100, to obtain the temporal (time) change information of the interlayer reflective wave Wr2 contained in the whole reflective wave Wr. This change information is, as described above, information used to evaluate the distribution of the porosities 102 contained in the composite material 100, in the thickness direction of the composite material 100. The specific configuration of the time-frequency analyzing unit 12 is not particularly limited. The time-frequency analyzing unit 12 may be configured as a known logic circuit or the like, including a switching element, a subtracter, a comparator, etc., or as a configuration realized by the operation of a known processor (CPU or the like) according to the programs stored in a storage unit (memory), namely, the functional configuration of the processor.

The specific method of the time-frequency analysis is not particularly limited. In the present embodiment, as will be described in the example later, short-time Fourier transformation (STFT) is employed. Parameters used to execute the STFT are not particularly limited. In the example described later, a temporal range in which the STFT is performed, division number of the temporal range, the kind of a window function, the width of the window function, etc., are set appropriately.

The display information generation unit 13 generates display information from the change information obtained by the time-frequency analyzing unit 12. The specific configuration of the display information generation unit 13 is not particularly limited. It is sufficient that the display information generation unit 13 is a known processor (CPU, or the like) for displaying an image on the display unit 14. Each of the time-frequency analyzing unit 12 and the display information generation unit 13 may be a functional configuration in which a single processor operates according to programs.

The display unit 14 displays the change information in the form of image information, numeric value information, etc., based on the display information generated in the display information generation unit 13. The specific configuration of the display unit 14 is not particularly limited, and a known liquid crystal display, or the like may be suitably used.

Figure 5:
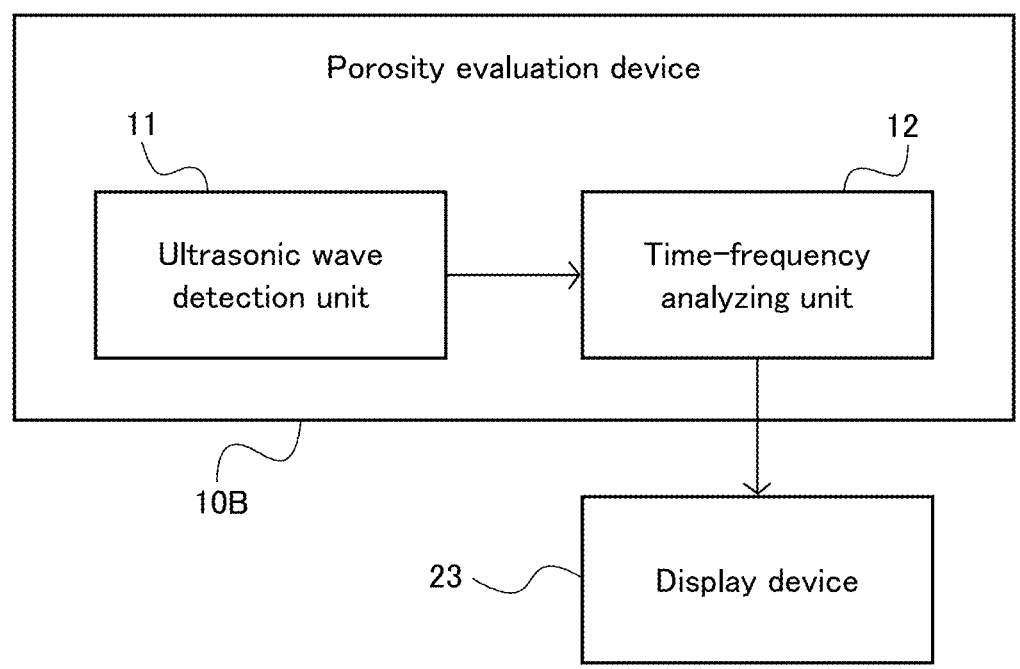
FIG. 5 is a block diagram showing the modified example of the porosity evaluation device of FIG. 4.

As shown in FIG. 5, in the present invention, a porosity evaluation device 10B may include only the ultrasonic wave detection unit 11 and the time-frequency analyzing unit 12 in the example of FIG. 5, the probe 111 and the ultrasonic transducer 112 are collectively shown as the block of the ultrasonic wave detection unit 11). The porosity evaluation device 10B of FIG. 5 does not include the display unit 14 (and the display information generation unit 13). As shown in FIG. 5, an external display device 23 may be connected to the porosity evaluation device 10B. Further, the porosity evaluation device 10A or 10B of the present invention may include an analyzing unit different from the time-frequency analyzing unit 12, although this not shown. Specifically, the analyzing unit may be, for example, a known unit which performs analysis, evaluation, test, etc., of the composite material 100, based on information relating to a matter different from the evaluation of the porosities.

The porosity evaluation device 10A or 10B according to the present embodiment is configured to display the change information on the display unit 14 or the display device 23. Therefore, in the above-described step S13, an operator (operator of the test of the composite material 100) of the porosity evaluation device 10A or 10B evaluates the porosities based on the image information or the like displayed on the display unit 14, 23. As a matter of course, the porosity evaluation device 10A or 10B may include a porosity evaluation unit to allow the porosity evaluation device 10A or 10B to evaluate the porosities, which will be described in Embodiment 2 described later.

As described above, the porosity evaluation method and the porosity evaluation device according to the present embodiment can evaluate well the distribution state of the porosities contained in the composite material, in the thickness direction of the composite material. Therefore, for example, the porosity levels of a plurality of members made of the composite material and integrally molded can be evaluated well for each of the different members. For example, in the case of aircraft member, as described above, there is a difference in permissibility of reduction of a strength, depending on the kind or role of the member. By using the porosity evaluation method of the present invention, the porosities are evaluated for each member and reduction of a strength attributed to the porosities is evaluated. This makes it possible to evaluate the members better and more efficiently.

Embodiment 2

In the porosity evaluation method (and the porosity evaluation device 10A, 10B) according to Embodiment 1, the distribution of the porosities 102 in the thickness direction of the composite material 100, is evaluated based on the reflective wave from the composite material 100. In contrast, in the porosity evaluation method according to Embodiment 2, the distribution of the porosities 102 contained in the composite material 100 is estimated more accurately based on the reflective wave from the composite material 100 and using a numeric value simulation. Hereinafter, the porosity evaluation method of the present embodiment will be specifically described with reference to FIG. 6.

[Porosity Evaluation Method]

Figure 6:
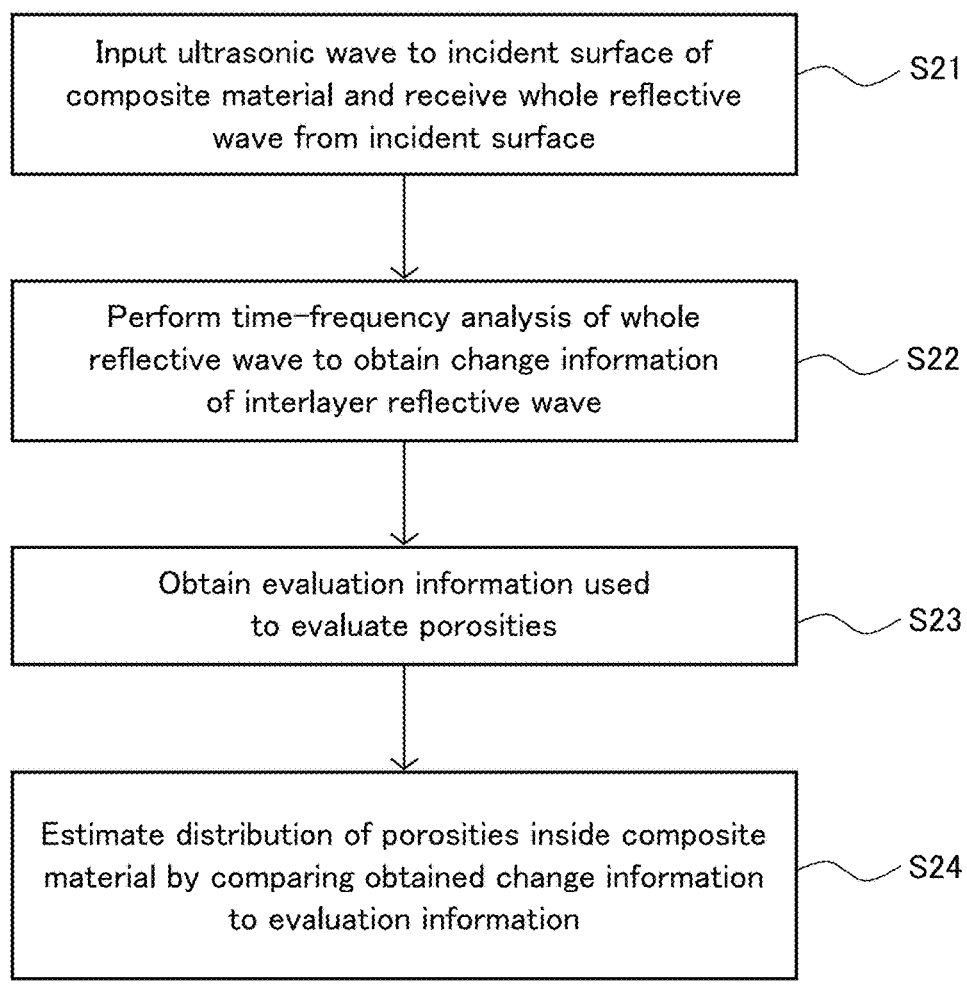
FIG. 6 is a view showing the steps of an exemplary porosity evaluation method of the composite material according to Embodiment 2 of the present invention.

As shown in FIG. 6, the step S21 and the step S22 of the porosity evaluation method according to the present embodiment are the same as the step S11 and the step S12 of the porosity evaluation method according to Embodiment 1, and the porosity evaluation method according to the present embodiment is differentiated from the porosity evaluation method according to Embodiment 1 in that the porosity evaluation method according to the present embodiment includes the step S23 and the step S24.

In the porosity evaluation method of FIG. 6, as in Embodiment 1, initially, the ultrasonic wave is input to the incident surface 103 of the composite material 100 in the thickness direction of the composite material 100, and the whole reflective wave Wr of the ultrasonic wave is received from the incident surface 103 (step S21). Then, the received whole reflective wave Wr is subjected to the time-frequency analysis, to obtain temporal change information of the interlayer reflective wave Wr2 contained in the whole reflective wave Wr (step S22).

Further, in the present embodiment, the evaluation information used to evaluate the porosities is obtained (step S23). Then, the obtained chance information is compared to the evaluation information, to estimate the distribution of the porosities 102 inside the composite material 100 (step S24).

The specific information obtained in the step S23 is not particularly limited. Typically, the evaluation information includes (1) simulated change information (simulated reproduction result) of the interlayer reflective wave Wr2 obtained by performing numeric value simulation which reproduces in a simulated manner the defective composite material 100B or 100C containing the porosities 102 which are molded, and input of the ultrasonic wave and reception of the reflective wave, with respect to the defective composite material 100B or 100C, and (2) known information of the interlayer reflective wave Wr2 which is obtained by input of the ultrasonic wave and reception of the reflective wave, with respect to a test piece of the composite material 100 containing known porosities 102. Hereinafter, for easier understanding of the description, the former (1) will be referred to as "simulated change information" and the latter (2) will be referred to as "known information."

Initially, how to obtain the (1) simulated change information will be described. As the numeric value simulation for obtaining the simulated change information, a known method can be suitably used. The specific method of the numeric value simulation is not particularly limited. In the example which will be described later, in the numeric value simulation, the simulated reproduction of the defective composite material 100B or 100C is performed in such a manner that the porosities 102 are modeled as a rectangular cross-section in which side lengths are distributed according to Gaussian distribution, and distributed randomly within the cross-section of the simulated defective composite material 100B or 100C. The simulated reproduction of input of the ultrasonic wave and reception of the reflective wave, with respect to the defective composite material 100B or 100C, is performed by a finite element method (FEM) using the actual incident waveform of the ultrasonic wave.

The numeric value simulation may be performed every time with reference to the actual change information obtained in the step S22, when the porosities of the composite material 100 are evaluated. Or, the numeric value simulation may be performed in advance plural times to create a database. Further, the numeric value simulation may be performed every time based on the actual change information after the step S22, and the resulting reproduction result may be registered in a database. In other words, the database of the result of the numeric value simulation may be constructed step by step concurrently with the evaluation of the porosities. In a case where the database is constructed step by step, the numeric value simulation may be performed under typical conditions to create a preliminary database, before the evaluation of the porosities starts.

Next, how to obtain the (2) known information will be described. The method of creating the test piece from which the known information is obtained is not particularly limited, and the defective composite material 100B or 100C may be created by a known method, in order to reveal the distribution state of the porosities 102 in advance. Instead of creating the test piece for the purpose of evaluation, the result of estimation (result of evaluation) of the distribution of the porosities 102 obtained by the porosity evaluation method of the present embodiment may be stored and used as the known information. In this case, the composite material 100 which is an evaluation target corresponds to the test piece from which the known information is obtained. The known information obtained from the test piece may be stored in the database and read as necessary as in the (1) simulated change information.

The porosity evaluation method of the present embodiment is not limited to the four steps of FIG. 6. For example, although the step S23 of obtaining the evaluation information is performed after the step S22 of obtaining the actual change information, the evaluation information may be obtained first (the step S23 is performed first) and then the actual change information may be obtained (the step S21 and the step S22 are performed thereafter). Further, the porosity evaluation method may further include the steps which are different from the steps S21 to S24.

As described above, in the step S23, irrespective of whether the evaluation information is the (1) simulated change information or the (2) known information, the information stored in the database can be read appropriately and used. In a case where the evaluation information is the (1) simulated change information, the result of simulation may be read appropriately from the database without performing the numeric value simulation, after the step S22 is performed. The database need not be prepared in a place where the porosity evaluation method is performed, but may be obtained from another place via a communication network. In this case, in the step S23, the evaluation information is obtained via the communication. As described above, the method of obtaining the evaluation information in the step 323 is not particularly limited.

Further, the evaluation information used in the step S24 may be one or two kinds of information. For example, in the step S24, the change information actually obtained may be compared to the (1) simulated change information, or to the (2) known information. Or, the change information actually obtained may be compared to both of the (1) simulated change information and the (2) known information. Or, the change information actually obtained may be compared to each of three or more kinds of information, if one or more kinds of information different from the (1) simulated change information and the (2) known information can be used as the evaluation information.

[Porosity Evaluation Device]

The specific configuration for carrying out the porosity evaluation method according to the present embodiment is not particularly limited. As in the case of the above-described Embodiment 1, an example of a typical porosity evaluation device (porosity evaluation device according to Embodiment 2) the carrying out the porosity evaluation method according to the present embodiment will be specifically described with reference to FIGS. 7, 8 and 9.

Figure 7:
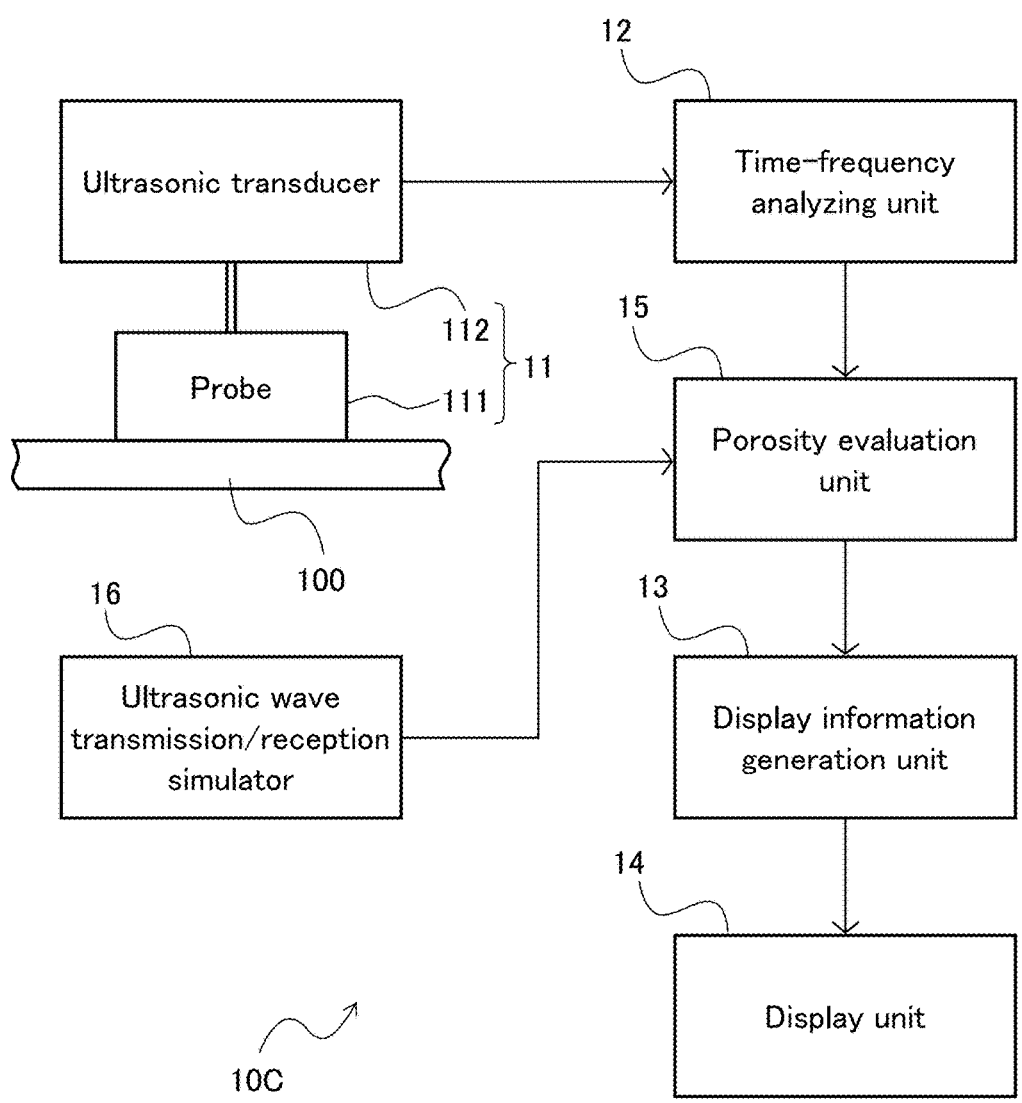
FIG. 7 is a block diagram schematically showing an exemplary porosity evaluation device used to perform the porosity evaluation method of FIG. 6.
Figure 8:
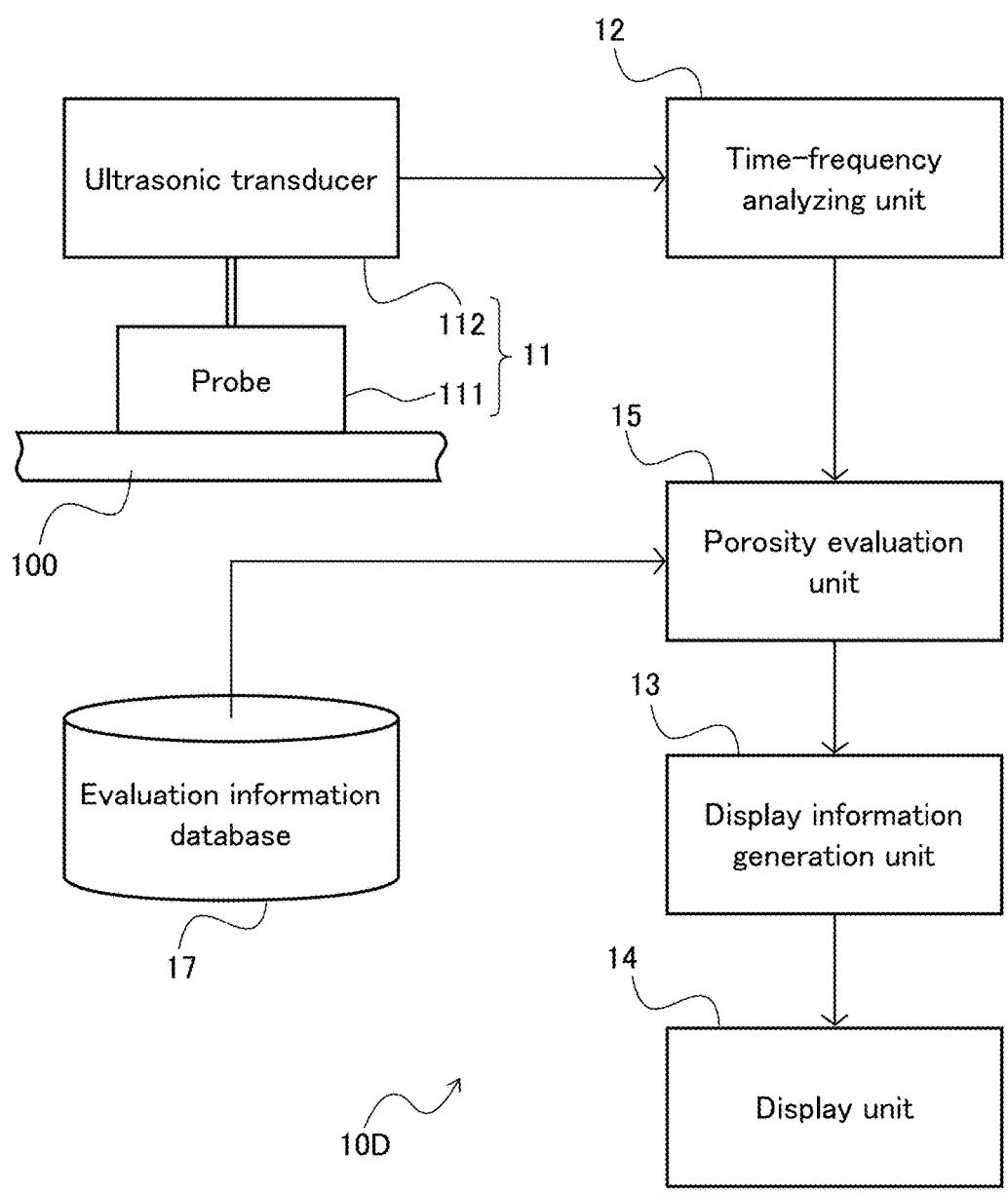
FIG. 8 is a block diagram showing the modified example of the porosity evaluation device of FIG. 7.

As shown in FIG. 7 or 8, a porosity evaluation device 10C or 10D according to the present embodiment has fundamentally the same configuration as that of the porosity evaluation device 10A or 10B of Embodiment 1, except that the porosity evaluation device 10C or lap includes at least a porosity evaluation unit 15.

The porosity evaluation unit 15 estimates the distribution of the porosities 102 inside the composite material 100 by comparing the change information obtained by the above-described time-frequency analyzing unit to the above-described evaluation information. As the evaluation information, as described above, the (1) simulated change information or the (2) known information, or both of the (1) simulated change information and the (2) known information (or other information in addition to the (1) simulated change information and the (2) known information), may be used. These evaluation information is obtained from an ultrasonic wave transmission/reception simulator 16 (only the simulated change information) of FIG. 7, or from an evaluation information database 17 (at least one of the simulated change information and the known information) of FIG. 8.

The specific configuration of the porosity evaluation unit 15 is not particularly limited. The porosity evaluation unit 15 may be configured as a known logic circuit or the like, including a switching element, a subtracter, a comparator, etc., or as a functional configuration realized by the operation of a known processor according to the programs. The porosity evaluation performed by the porosity evaluation unit 15 is not limited to the above-described evaluation in the step S24, namely, the evaluation for estimating the distribution of the porosities 102 by comparing the actual change information to the evaluation information, and may be other known evaluation method.

In the porosity evaluation device 10C of FIG. 7, the porosity evaluation unit 15 is configured to obtain the simulated change information from the ultrasonic wave transmission/reception simulator 16. Therefore, the porosity evaluation device 10C corresponds to the configuration in which the numeric value simulation is performed every time, of the above-described porosity evaluation methods. The ultrasonic wave transmission/reception simulator 16 is configured to perform the numeric value simulation for obtaining the above-described simulated change information. The specific configuration of the ultrasonic wave transmission/reception simulator 16 is not particularly limited. The ultrasonic wave transmission/reception simulator 16 may be a functional configuration realized by the operation of a known processor according to the programs of the numeric value simulation.

In contrast, in the porosity evaluation device 10D of FIG. 8, the porosity evaluation unit 15 is configured to obtain at least one of the simulated change information and the known information, from the evaluation information database 17. Therefore, the porosity evaluation device 101) corresponds to the configuration in which the result of reproduction is obtained from the database, of the above-described porosity evaluation methods. The specific configuration of the evaluation information database 17 is not particularly limited. It is sufficient that the evaluation information database 17 is a known memory or the like which is able to store the database.

Figure 9:
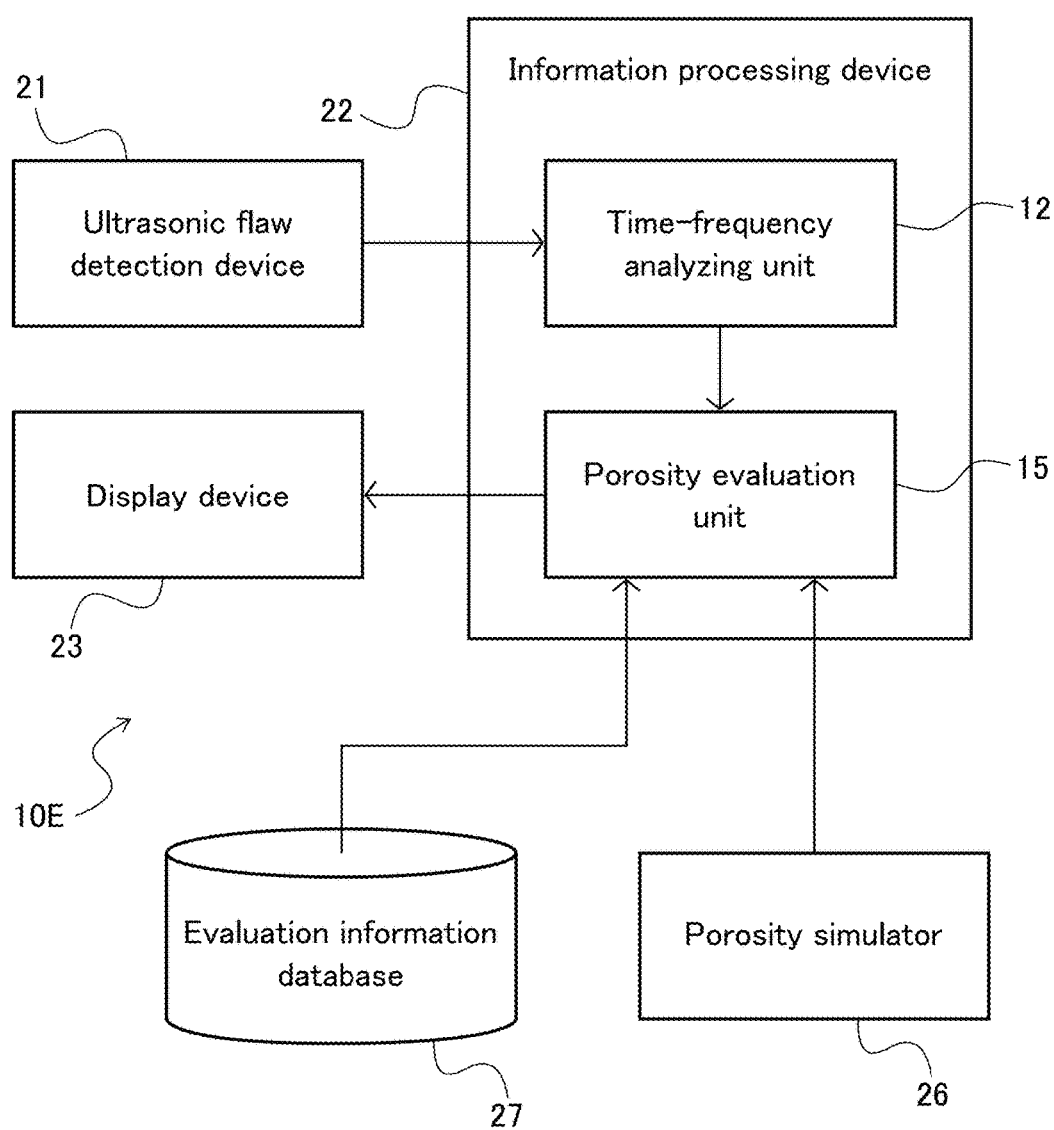
FIG. 9 is a block diagram showing the modified example of the porosity evaluation device of FIG. 7 or 8.

The porosity evaluation device 10C of FIG. 7 includes only the ultrasonic wave transmission/reception simulator 16, while the porosity evaluation device 10D of FIG. 8 includes only the evaluation information database 17. However, the present invention is not limited to this. As shown in FIG. 9, a porosity evaluation device 10E includes both of an ultrasonic wave transmission/reception simulator 26 and an evaluation information database 27.

The porosity evaluation device 10E of FIG. 9 is configured as a "porosity evaluation system" which uses a known ultrasonic flaw detection device 21 and a known information processing device. As the known ultrasonic flaw detection device 21, for example, there are a test unit which tests defects different from the porosities 102, a test unit which evaluates the porosities (evaluates the total amount of porosities) in a conventional manner, etc. As the known information processing device 22, for example, there is a computer, but the known information processing device 22 is not particularly limited. Therefore, the "porosity evaluation device" of the present invention is not limited to the single "evaluation device" of FIGS. 4, 5, 7 and 8, and includes the "evaluation system" in which the "plurality of units" are connected to each other.

In the example of FIG. 9, as in the porosity evaluation device 10B of FIG. 5, the porosity evaluation device 10E includes the external display device 23. However, the porosity evaluation device 10E may be configured in such a manner that the information processing device 22 includes the display unit 14, as in the porosity evaluation device 10A of FIG. 4, the porosity evaluation device 10C of FIG. 7 or the porosity evaluation device 10D of FIG. 8.

Further, in the example of FIG. 9, the ultrasonic wave transmission/reception simulator 26 and the evaluation information database 27 are not included in the porosity evaluation device 10C of FIG. 7 or the porosity evaluation device 10D of FIG. 8, but are connected to the information processing device 22 as independent "devices." Therefore, the ultrasonic wave transmission/reception simulator 16 may not be included in the porosity evaluation device 10C of FIG. 7, and the evaluation information database 17 may not be included in the porosity evaluation device 10D of FIG. 8. Instead, the ultrasonic wave transmission/reception simulator 16 may be externally provided for the porosity evaluation device 10C of FIG. 7, and the evaluation information database 17 may be externally provided for the porosity evaluation device 10D of FIG. 8.

As described above, in the porosity evaluation method and the porosity evaluation device of the present embodiment, the result of actual measurement is compared to the result of simulated reproduction by the numeric value simulation (the simulated change information). Therefore, it becomes possible to more accurately evaluate the porosity level of the member made of the composite material. As a result, the accuracy of evaluation of the member can be improved, and the accuracy of evaluation of reduction of a strength attributed to the porosities can be improved.

Each of the above-described porosity evaluation devices 10C to 10E of the present embodiment includes the porosity evaluation unit 15 which compares the result of actual measurement to the result of simulated reproduction by the numeric value simulation. However, the present invention is not limited to this. As described above, each of the above-described porosity evaluation devices 10C to 10E may evaluate the distribution of the porosities 102 by other evaluation methods. Or, as in the above-described Embodiment 1, the operator of each of the above-described porosity evaluation devices 10C to 10E may perform further evaluation based on the result (displayed on the display unit 14 as the image information or the like) of evaluation performed by the porosity evaluation unit 15. Further, two or more kinds of porosity evaluation units 15 may be provided instead of one kind of porosity evaluation unit 15.

Example

Example and comparative example of the present invention will be specifically described. The present invention is not limited to the example and the comparative example. A person skilled in the art can change, modify, and alter the present invention within a scope of the invention. A measurement method or an analyzing method in the example and the comparative example described below were performed as follows.

(Measurement of Reflective Wave from Sample)

Using LexScan manufactured by INSITE Co., Ltd. and a water immersion probe with a nominal center frequency of 10 MHz, an ultrasonic pulse was input to one of the surfaces or the other surface of a porosity evaluation sample or a sound comparative sample, and the reflective wave was received.

(Time-Frequency Analysis of Reflective Wave)

Measurement time waveform of the reflective wave of the ultrasonic wave obtained from the porosity evaluation sample or the sound comparative sample was subjected to the short-time Fourier transformation (STFT), and time-frequency response was graphically represented and analyzed. In this case, the temporal (time) range of the STFT, and the kind and width of the window function were appropriately set, according to a frequency range and temporal range which were to be noted. In the graphical representation, the time waveforms were discretized and numerically converted, in each sampling sample.

(Analysis by Numeric Value Simulation)

By performing the numeric value simulation using an implicit method based on the finite element method (FEM) disclosed in ISHII, Yosuke and BIWA, Shiro, Journal of Applied Physics 111, No. 084907 (2012), the numeric value simulation was performed, to analyze the reflective wave of the ultrasonic wave obtained from the porosity evaluation sample or the sound comparative sample. In the numeric value simulation, the incident waveform used in the measurement of the reflective wave was simulated and used. The incident waveform was wide bandwidth wave with a center frequency of about 7 MHz.

Example

A composite material for aircraft UTS50/135 (product name) manufactured by Toho Tenax Co., Ltd., was cured under curing conditions (autoclave conditions) in which the degree of vacuum was 750 mmHg, no pressurization was applied, and the curing temperature was 180 degrees C., to create the porosity evaluation sample of 1.20 mm×100 mm with the number of laminated layers (number of plies) of 24 (the thickness of the whole laminated layers was about 4.6 mm). Two kinds of laminated structures were created, which were the laminated specimen ($[0]_{24}$) in which the fiber directions of the 24 plies were the same and the quasi-isotropic laminated structure ($[45/0/-45/90]_{3s}$) in which fiber directions were 0 degree, 90 degrees, 45 degrees and −45 degrees which were uniformly distributed. Carbon fibers used in UTS50/135 were UD (Uni-direction) material of UTS50 (product name) manufactured by Toho Tenax Co., Ltd, and matrix material used in UTS50/135 was a highly tough epoxy resin manufactured by Toho Tenax Co., Ltd.

The obtained porosity evaluation sample imitated a defective composite material in which a half of the part which was closer to one of the surfaces (obverse surface) contained 4% of porosities, and the other half which was closer to the other surface (reverse surface) contained no porosities (see FIG. 1A). Therefore, the total amount of the porosities contained. In the whole of the porosity evaluation sample was 2%.

As described above, the ultrasonic wave was input to the obverse surface (the surface which is closer to a region containing the porosities) of the obtained porosity evaluation sample and the reflective wave was measured, while the ultrasonic wave was also input to the reverse surface (the surface closer to a sound region containing no porosities) and the reflective wave was measured. The results for the porosity evaluation sample, having the quasi-isotropic laminated structure are shown in "Example (obverse surface)" and "Example (reverse surface)" of FIG. 10.

Figure 11A:
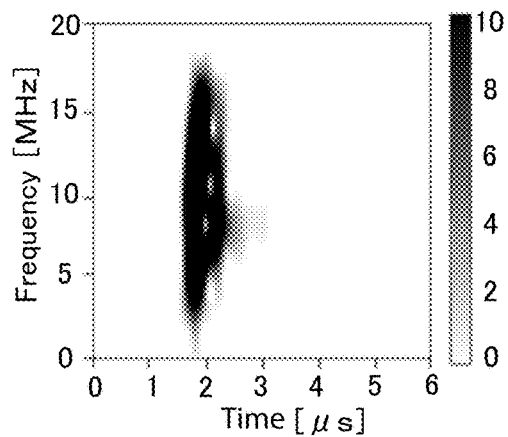
FIGS. 11A to 11D are graphs showing the results of the example of the present invention, and the results of time-frequency analysis of the reflective waves obtained from the porosity evaluation sample.

The reflective wave measured at the obverse surface or the reverse surface was subjected to the time-frequency analysis and graphically represented, in the above-described manner. The results are shown in FIG. 11A (result of analysis for the region which is closer to the obverse surface) and FIG. 11B (result of analysis for the region which is closer to the reverse surface).

Figure 12A:
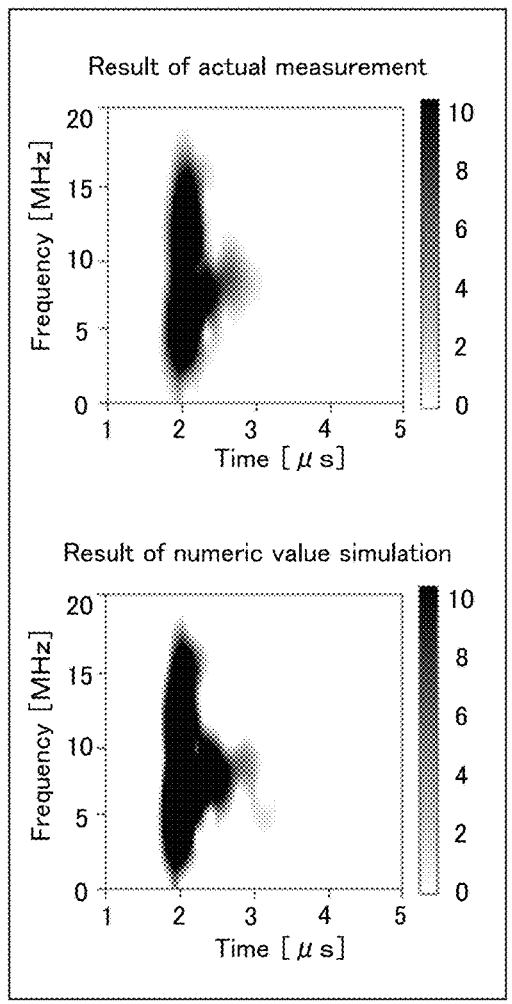
FIGS. 12A and 12B are graphs showing the results of the example of the present invention, and a comparison between the results of time-frequency analysis of the reflective waves obtained from the porosity evaluation sample and the results of numeric value simulation of the reflective waves.
Figure 12B:
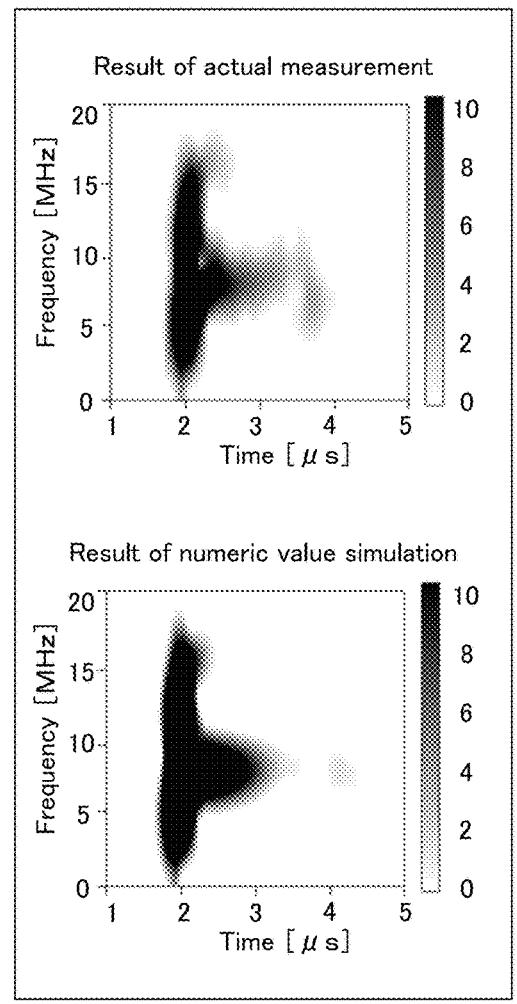

By the above-described numeric value simulation, the reflective wave at the obverse surface and the reflective wave at the reverse surface, of the porosity evaluation sample, were reproduced and graphically represented. In this numeric value simulation, the porosities were modeled as a rectangular cross-section in which the average value was 0.1 mm×0.2 mm, and side lengths were distributed according to Gaussian distribution, in the whole of the cross-section of the porosity evaluation sample in such a manner that the porosities were distributed unevenly to be present in a region which is closer to the obverse surface (see FIG. 1C). The results are shown in FIG. 12A (result of analysis for the region which is closer to the obverse surface) and FIG. 12B (result of analysis for the region which is closer to the reverse surface). In FIGS. 12A and 12B, the upper graphs indicate the results of actual measurement, and the lower graphs indicates the results of the numeric value simulation.

Comparative Example

The sound comparative sample of 1.20 mm 100 mm and the number of laminated layers (number of plies) of 24 (the thickness of the whole plies was about 4.6 mm) was created under the same conditions as those of the Example, except that the porosities contained no porosities and a molding pressure was set to 400 kPa.

For the obtained sound comparative sample, the ultrasonic wave was input to the obverse surface or the reverse surface, and the reflective wave was measured, as in the Example. Of the obtained results, the results of the porosity evaluation sample having the quasi-isotropic laminated structure were shown in "Comparative Example (obverse surface)" and "Comparative Example (reverse surface)" of FIG. 10.

The reflective wave measured at the obverse surface and the reflective wave measured at the reverse surface were subjected to the time-frequency analysis and graphically represented as described above. The results are shown in FIG. 11C (result of analysis for the region which is closer to the obverse surface) and FIG. 11D (result of analysis for the region which is closer to the reverse surface).

Comparison or the Like Between Example and Comparative Example

Figure 10:
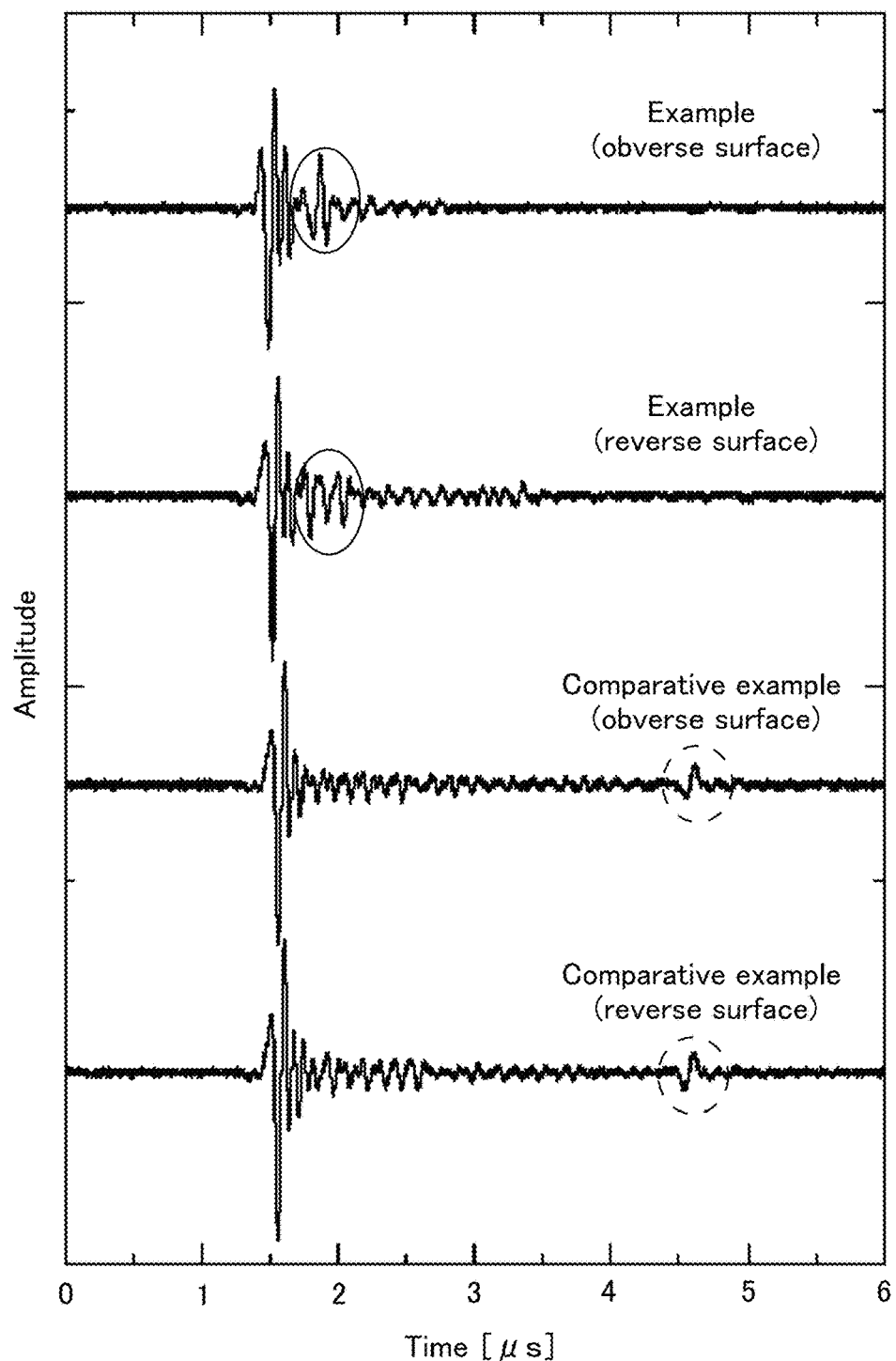
FIG. 10 is a diagram showing the results of the example of the present invention, and the waveforms of reflective waves obtained from a porosity evaluation sample.

As shown in FIG. 10, regarding the whole reflective wave Wr at each of the obverse surface and the reverse surface, of the porosity evaluation sample, the interlayer reflective wave Wr2 (portion surrounded by a solid-line circle, near 1.8 to 2.2 μs) following the obverse surface reflective wave Wr0 (near 1.6 to 1.7 μs) was observed, and an oscillation of the interlayer reflective wave in the case where the ultrasonic wave was input to the obverse surface disappeared at a relatively earlier time. In contrast, regarding the whole reflective wave Wr at each of the Obverse surface and the reverse surface, of the sound comparative sample, the bottom surface reflective wave Wr1 (portion surrounded by a broke-line circle, near 4.6. μs) was observed, whereas the bottom surface reflective wave Wr1 was not observed in the porosity evaluation sample.

Figure 11B:
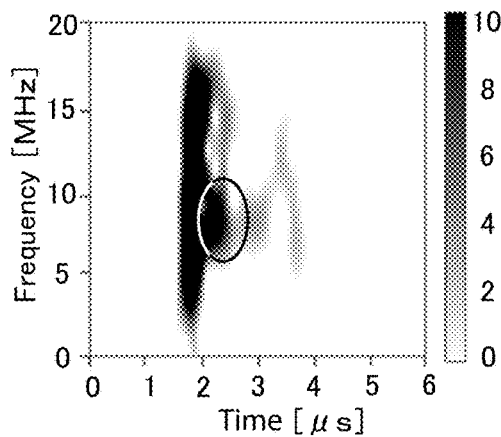
Figure 11C:
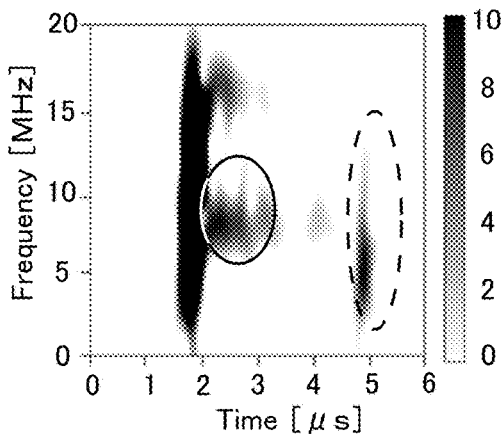
Figure 11D:
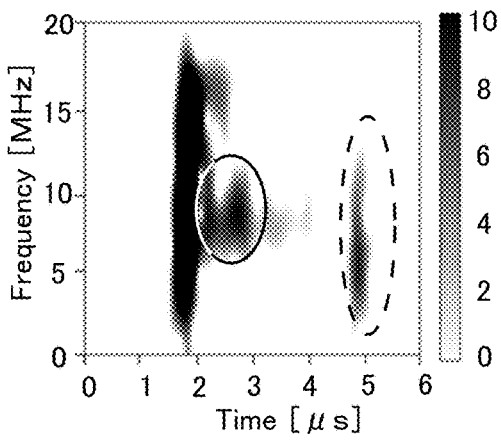

As shown in FIGS. 11C and 11D, as a result of the time-frequency analysis, signals (regions surrounded by broken-line circles), corresponding to the bottom surface reflective wave Wr1, were observed in the sound comparative sample, as in the results of FIG. 10. On the other hand, as shown in FIGS. 11A and 11B, as a result of the time-frequency analysis, signals corresponding to the bottom surface reflective wave Wr1 were not observed in the porosity evaluation sample.

Regarding the sound comparative sample, a continued oscillation of a component with a frequency of about 8 MHz, following the obverse surface reflective wave Wr0, at each of the obverse surface (FIG. 11C) and the reverse surface (FIG. 11D), was observed, as indicated by a region surrounded by a solid-line circle. Regarding the porosity evaluation sample, a continued oscillation of a component with a frequency of about 8 MHz, was observed, as indicated by a region surrounded by a solid-line circle of FIG. 11B, in the case where the ultrasonic wave was input to the reverse surface which was closer to the sound region containing no porosities. On the other hand, regarding the porosity evaluation sample, a continued oscillation of a component with a frequency of about 8 MHz, was not sufficiently observed, as shown in FIG. 11A, in the case where the ultrasonic wave was input to the obverse surface which was closer to the region in which the porosities were present.

FIGS. 11A to 11D show the results of the porosity evaluation sample having the quasi-isotropic laminated structure. However, results indicating similar trends were obtained regarding the porosity evaluation sample having the laminated structure with the same fiber direction, although they are not shown.

As should be understood from the above, regardless of whether the ultrasonic wave was input to the obverse surface or the reverse surface of the porosity evaluation sample, the bottom surface reflective wave Wr1 was not observed, and a difference in the component of the continued oscillation following the obverse surface reflective wave was observed. In view of this, the whole reflective wave is subjected to the time-frequency analysis to obtain the temporal change information of the interlayer reflective wave. In this way, the distribution of the porosities contained in the composite material, in the thickness direction of the composite material, can be evaluated.

Regarding the porosity evaluation sample, when a comparison was made among the result of the numeric value simulation in the case where the ultrasonic wave was input to the obverse surface (the surface which is closer to the region in which the porosities were present), the result of the numeric value simulation in the case where the ultrasonic wave was input to the reverse surface (the surface which is closer to the sound region in which no porosities were present), and the result of the numeric value simulation in the case where the porosities were evenly (uniformly) present, the followings were found, although this is not shown. A continued oscillation following the obverse surface reflective wave Wr0 lasted the a longer time in the case where the ultrasonic wave was input to the reverse surface (the surface which is closer to the sound region in which no porosities were present) than in the case where the porosities were evenly present. Also, a continued oscillation following the obverse surface reflective wave Wr0 damped in a shorter time in the case where the ultrasonic wave was input to the obverse surface than in the case where the porosities were evenly present.

The upper graphs of FIGS. 12A and 12B indicate the results of the time-frequency analysis in the case where the reflective wave of the porosity evaluation sample was actually measured. The lower graphs of FIGS. 12A and 12B indicate the results of the simulated time-frequency analysis by the numeric value simulation. As is clear from a comparison between the upper and lower graphs, the results of the time-frequency analysis of the actually measured reflective wave, correspond favorably to the results of the time-frequency analysis by the numeric value simulation.

Therefore, the simulated change information of the interlayer reflective waves obtained by the numeric value simulation (or known information of the interlayer reflective waves obtained from the test piece whose porosity distribution is known) are created into the database, and the change information of the interlayer reflective wave actually measured is compared to the simulated change information (or known result of porosity evaluation). In this way, it becomes possible to accurately estimate the distribution of the porosities inside the composite material.

Numerous improvements and alternative embodiments of the invention will be apparent to those skilled in the art in view of the foregoing description. Accordingly, the description is to be construed as illustrative only, and is provided for the purpose of teaching those skilled in the art the best mode of carrying out the invention. The details of the structure and/or function may be varied substantially without departing from the spirit of the invention.

INDUSTRIAL APPLICABILITY

The present invention is widely suitably used in the fields of the evaluation of porosities contained in a fiber reinforced resin composite material. In particular, the present invention is suitably used in the evaluation of porosities of a composite material used in the field of aerospace which applies higher structural strength requirement.

REFERENCE SIGNS LIST 10A porosity evaluation device
10B porosity evaluation device
10C porosity evaluation device
10D porosity evaluation device
11 ultrasonic wave detection unit
12 time-frequency analyzing unit
13 display information generation unit
14 display unit
15 porosity evaluation unit
16 ultrasonic wave transmission/reception simulator
17 evaluation information database
21 ultrasonic flaw detection device
22 information processing device
23 display device
100 composite material
100A sound composite material
100B defective composite material
100C defective composite material
101 ply
102 porosities
103 incident surface
104 bottom surface
105 interlayer interface
111 probe
112 ultrasonic transducer
Wi incident wave
Wr whole reflective wave
Wr0 obverse surface reflective wave
Wr1 bottom surface reflective wave
Wr2 interlayer reflective wave

The invention claimed is:

1. A method of evaluating porosities contained in a composite material, the method comprising:
inputting an ultrasonic wave in a thickness direction of the composite material to an incident surface which is one of surfaces of the composite material and receiving a reflective wave from the incident surface, the composite material having a multi-layer structure which is obtained by laminating a plurality of plies of prepreg and curing the prepreg; and
performing time-frequency analysis of a whole reflective wave to obtain damping that is temporal change information of an interlayer reflective wave, the temporal change information being used to evaluate a distribution of the porosities contained in the composite material, in the thickness direction of the composite material, the whole reflective wave being the reflective wave received, and the interlayer reflective wave being a reflective wave included in the whole reflective wave and reflected on an interlayer interface of the multi-layer structure.

2. The method of evaluating the porosities contained in the composite material, according to claim 1,
wherein when an incident frequency of the ultrasonic wave which is used to evaluate a total amount of the porosities contained in the composite material based on damping of a bottom surface reflective wave reflected from a bottom surface which is the other surface of the composite material, is a standard frequency,
the incident frequency of the ultrasonic wave is set to be higher than the standard frequency.

3. The method of evaluating the porosities contained in the composite material, according to claim 1,
wherein the incident frequency is variable according to a thickness of the plies constituting the composite material.

4. The method of evaluating the porosities contained in the composite material, according to claim 1,
wherein to estimate the distribution of the porosities contained in the composite material, the change information of the interlayer reflective wave received actually is compared to evaluation information, and
wherein used as the evaluation information is,
at least one of:
simulated change information of the interlayer reflective wave, which is obtained by performing numeric value simulation which reproduces in a simulated manner the composite material containing the porosities which are modeled, and input of the ultrasonic wave and reception of the reflective wave, with respect to the composite material, and
known information of the interlayer reflective wave, which is obtained by input of the ultrasonic wave and reception of the reflective wave, with respect to a test piece of the composite material containing the porosities which are known.

5. A device for evaluating porosities contained in a composite material, the device comprising:
an ultrasonic wave detection unit which inputs an ultrasonic wave in a thickness direction of the composite material to an incident surface which is one of surfaces of the composite material and receives a reflective wave from the incident surface, the composite material having a multi-layer structure which is obtained by laminating a plurality of plies of prepreg and curing the prepreg; and
a time-frequency analyzing unit which performs time-frequency analysis of a whole reflective wave to obtain damping that is temporal change information of an interlayer reflective wave, the temporal change information being used to evaluate a distribution of the porosities contained in the composite material, in the thickness direction of the composite material, the whole reflective wave being the reflective wave received, and the interlayer reflective wave being a reflective wave included in the whole reflective wave and reflected on an interlayer interface of the multi-layer structure.

6. The device for evaluating the porosities contained in the composite material, according to claim 5, further comprising:

a display information generation unit which generates display information from the change information; and a display unit which displays the change information using the display information.

7. The device for evaluating the porosities contained in the composite material, according to claim 5, comprising:

a porosity evaluation unit which estimates the distribution of the porosities contained in the composite material, by comparing the change information obtained by the time-frequency analyzing unit to evaluation information, wherein used as the evaluation information is, at least one of simulated change information of the interlayer reflective wave and known information obtained in advance, of the interlayer reflective wave of the composite material, the simulated change information of the interlayer reflective wave being obtained by performing numeric value simulation which reproduces in a simulated manner, input of the ultrasonic wave and reception of the reflective wave, with respect to the composite material containing the porosities which are modeled, and the known information of the interlayer reflective wave being obtained by input of the ultrasonic wave and reception of the reflective wave, with respect to a test piece of the composite material containing the porosities which are known.

8. The device for evaluating the porosities contained in the composite material, according to claim 7, comprising:

at least one of an ultrasonic wave transmission/reception simulator which performs the numeric value simulation and an evaluation information database in which plural evaluation information is stored, wherein the porosity evaluation unit obtains the evaluation information from at least one of the ultrasonic wave transmission/reception simulator and the evaluation information database.

9. The method of evaluating the porosities contained in the composite material, according to claim 1, wherein an ultrasonic wave in a wide bandwidth including a frequency satisfying a formula $f=c/(2h)$ is used as an incident wave of the ultrasonic wave.

10. The device for evaluating the porosities contained in the composite material, according to claim 5, wherein an ultrasonic wave in a wide bandwidth including a frequency satisfying a formula $f=c/(2h)$ is used as an incident wave of the ultrasonic wave.

* * * * *